(12) United States Patent
Germain et al.

(10) Patent No.: US 8,794,811 B2
(45) Date of Patent: Aug. 5, 2014

(54) EDGE-ILLUMINATED FLAT PANEL AND LIGHT MODULE FOR SAME

(75) Inventors: Steve Germain, Quebec (CA); Sebastien Magnan, Quebec (CA)

(73) Assignee: GE Lighting Solutions, LLC, Cleveland, OH (US)

( * ) Notice: Subject to any disclaimer, the term of this patent is extended or adjusted under 35 U.S.C. 154(b) by 171 days.

(21) Appl. No.: 13/403,052

(22) Filed: Feb. 23, 2012

(65) Prior Publication Data

US 2012/0236598 A1 Sep. 20, 2012

Related U.S. Application Data

(60) Provisional application No. 61/453,299, filed on Mar. 16, 2011.

(51) Int. Cl.
*F21V 7/04* (2006.01)

(52) U.S. Cl.
USPC ............ 362/612; 362/611; 362/396; 362/399

(58) Field of Classification Search
USPC .................. 362/600, 603, 606, 396, 249.01, 362/249.03, 249.02; 40/546
See application file for complete search history.

(56) References Cited

U.S. PATENT DOCUMENTS

| 6,979,115 | B2 * | 12/2005 | Ohizumi et al. | 362/634 |
| 7,095,461 | B2 * | 8/2006 | Kim | 349/58 |
| 7,338,195 | B2 * | 3/2008 | Ogino et al. | 362/612 |
| 7,445,369 | B2 * | 11/2008 | Yu et al. | 362/612 |
| 7,481,563 | B2 * | 1/2009 | David et al. | 362/612 |
| 7,815,358 | B2 | 10/2010 | Inditsky | |
| 2007/0247870 | A1 | 10/2007 | Sakai et al. | |
| 2008/0219002 | A1 | 9/2008 | Sommers et al. | |
| 2008/0284308 | A1 * | 11/2008 | Pang | 313/498 |
| 2009/0244909 | A1 | 10/2009 | Chen | |
| 2011/0038149 | A1 | 2/2011 | Zlotnikov et al. | |
| 2011/0051457 | A1 | 3/2011 | Chen | |

FOREIGN PATENT DOCUMENTS

| EP | 1655536 A1 | 5/2006 |
| EP | 1744098 A1 | 1/2007 |
| GB | 2463027 A | 3/2010 |
| WO | 2006054855 A1 | 5/2006 |
| WO | 2010140103 A1 | 12/2010 |
| WO | WO 2010140103 A1 * | 12/2010 |

OTHER PUBLICATIONS

PCT Search Report and Written Opinion dated Jan. 24, 2013 from corresponding Application No. PCT/US2012/028867.

* cited by examiner

*Primary Examiner* — Ali Alavi

(74) *Attorney, Agent, or Firm* — Fay Sharpe LLP

(57) ABSTRACT

An apparatus comprising a transparent or translucent panel and a light module comprising a plurality of light emitting diode (LED) devices. The light module is mechanically connected to an edge of the panel with the LED devices oriented to inject light into the edge of the panel.

22 Claims, 28 Drawing Sheets

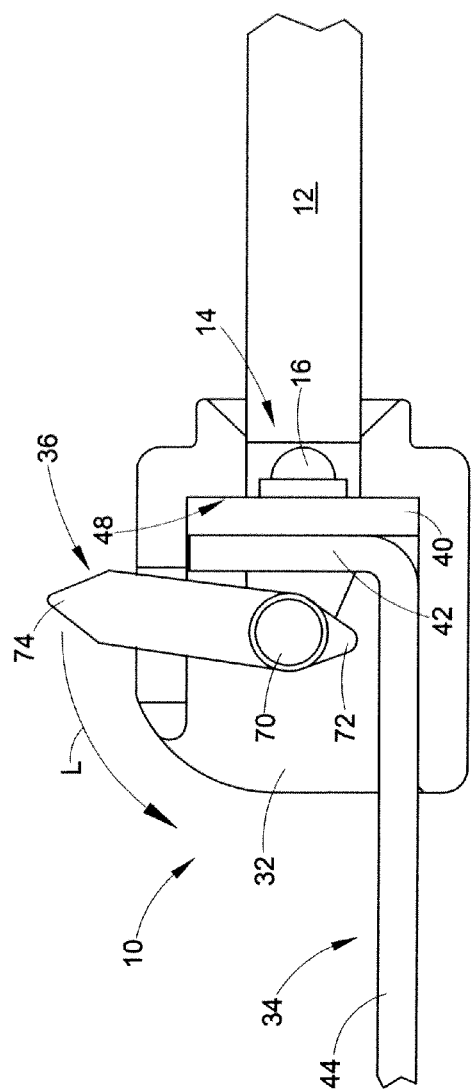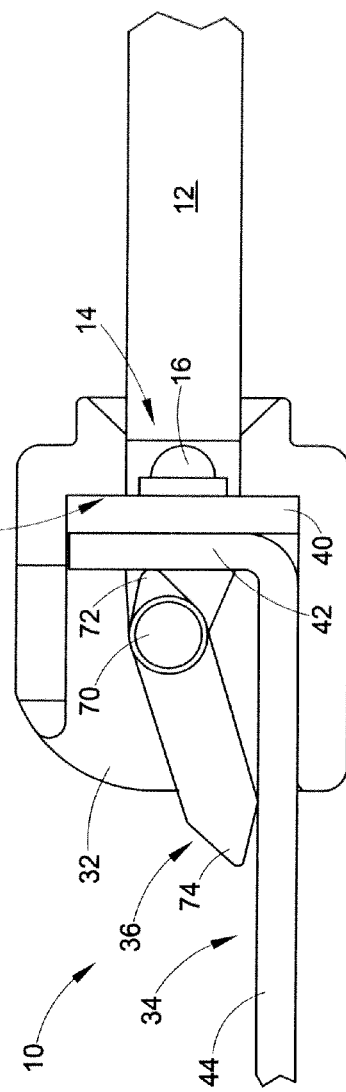

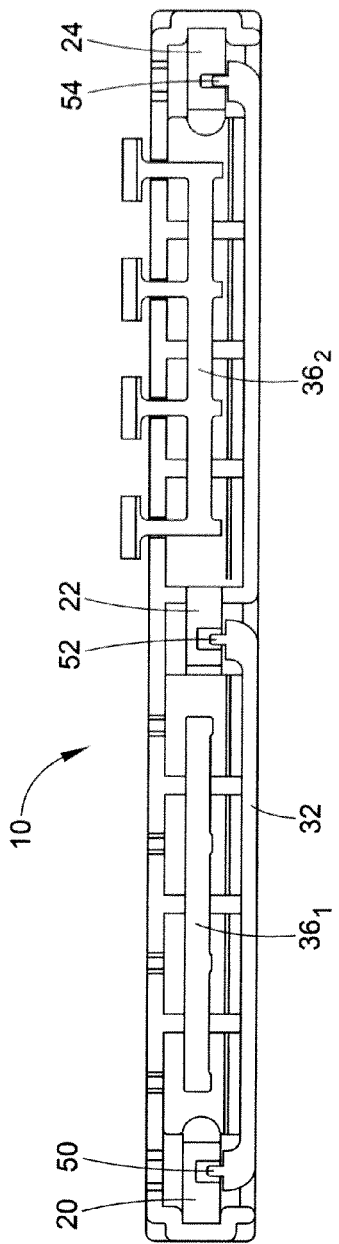
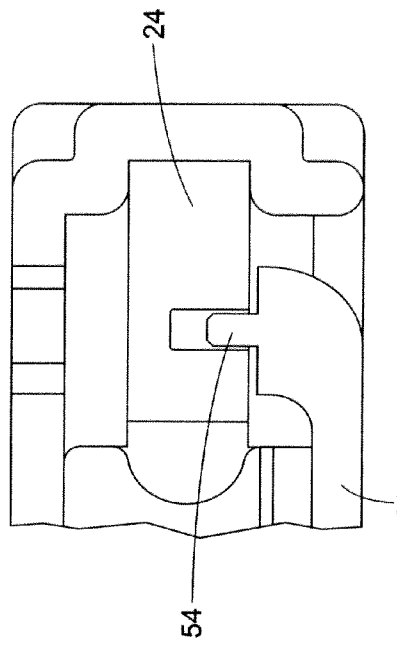
FIG. 11
FIG. 12

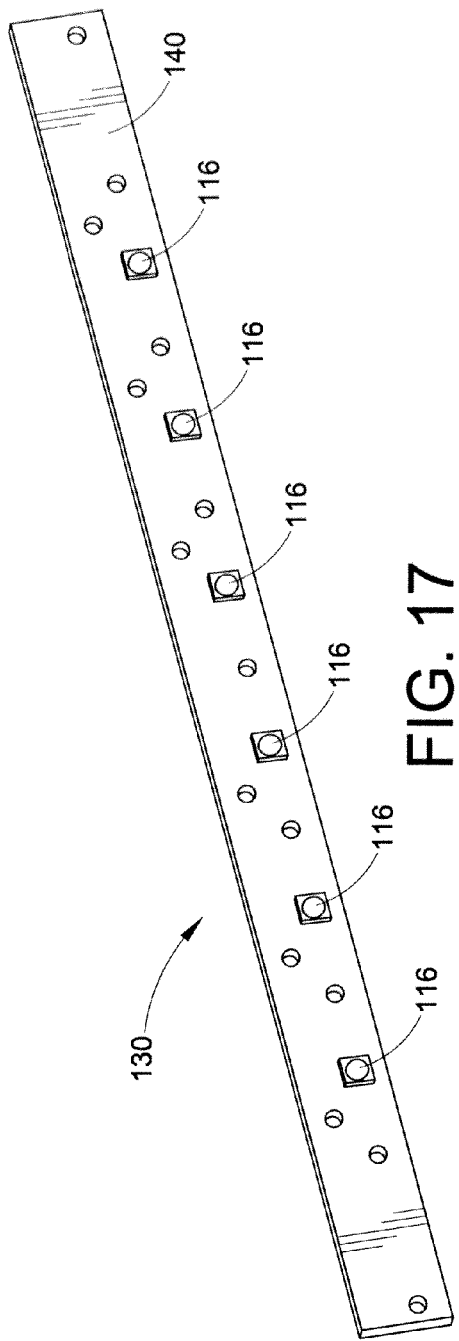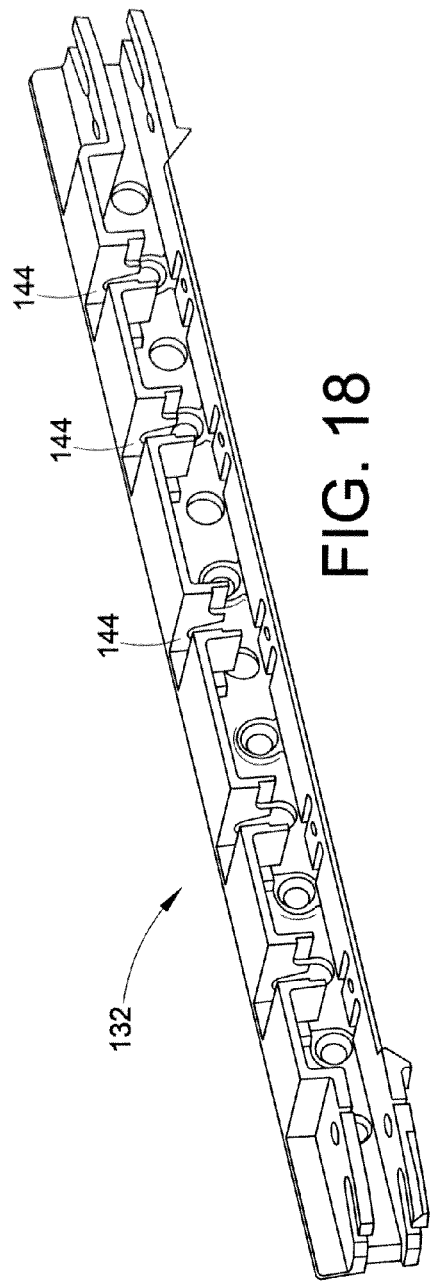

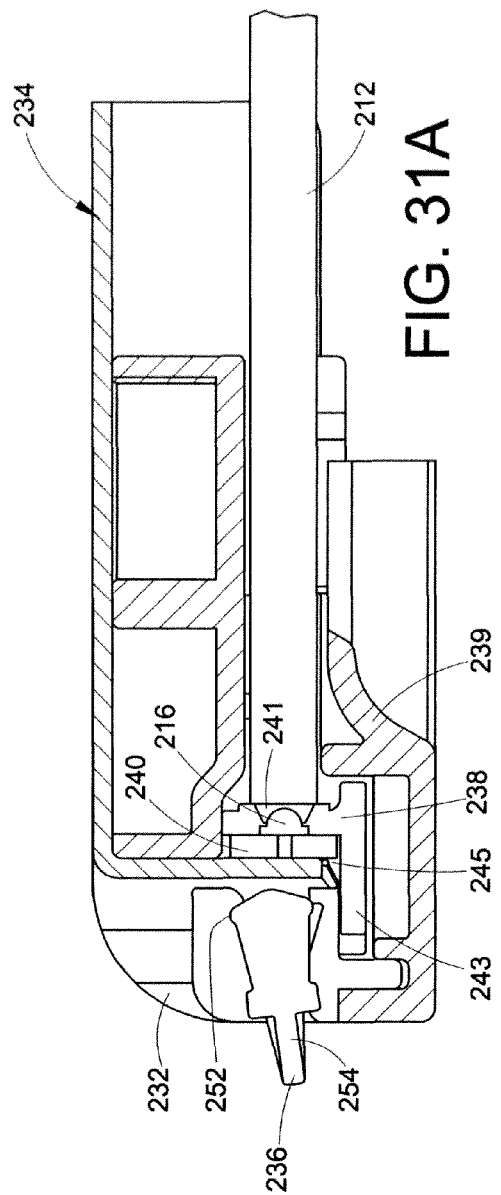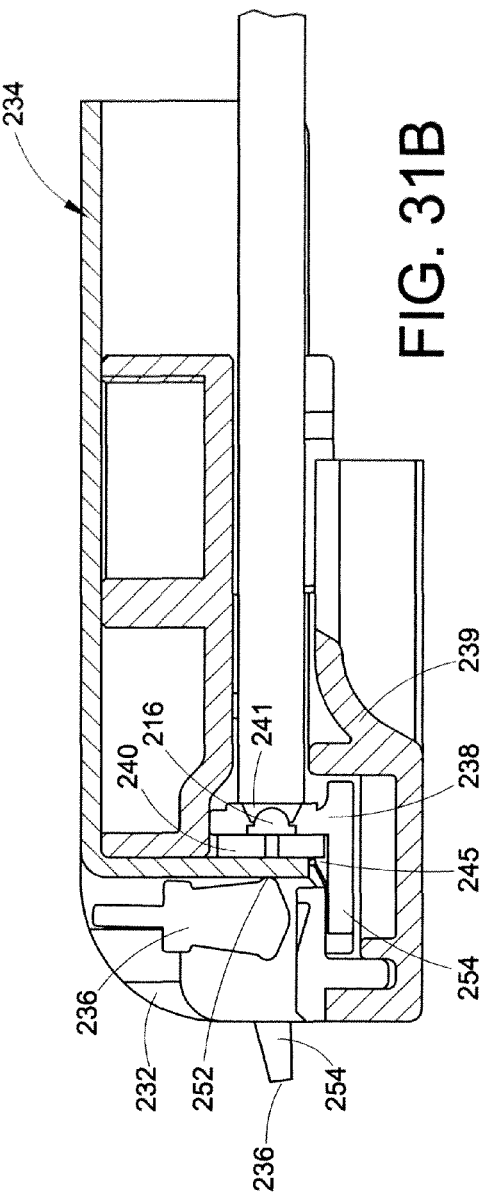

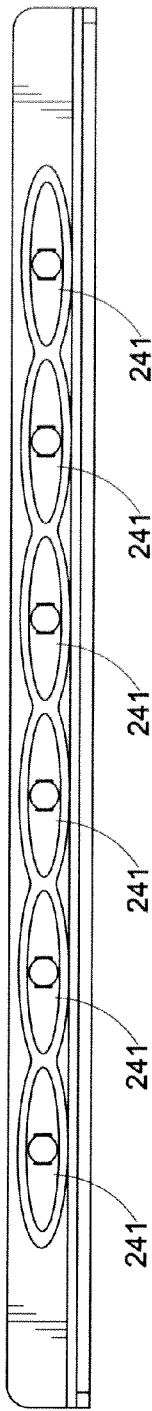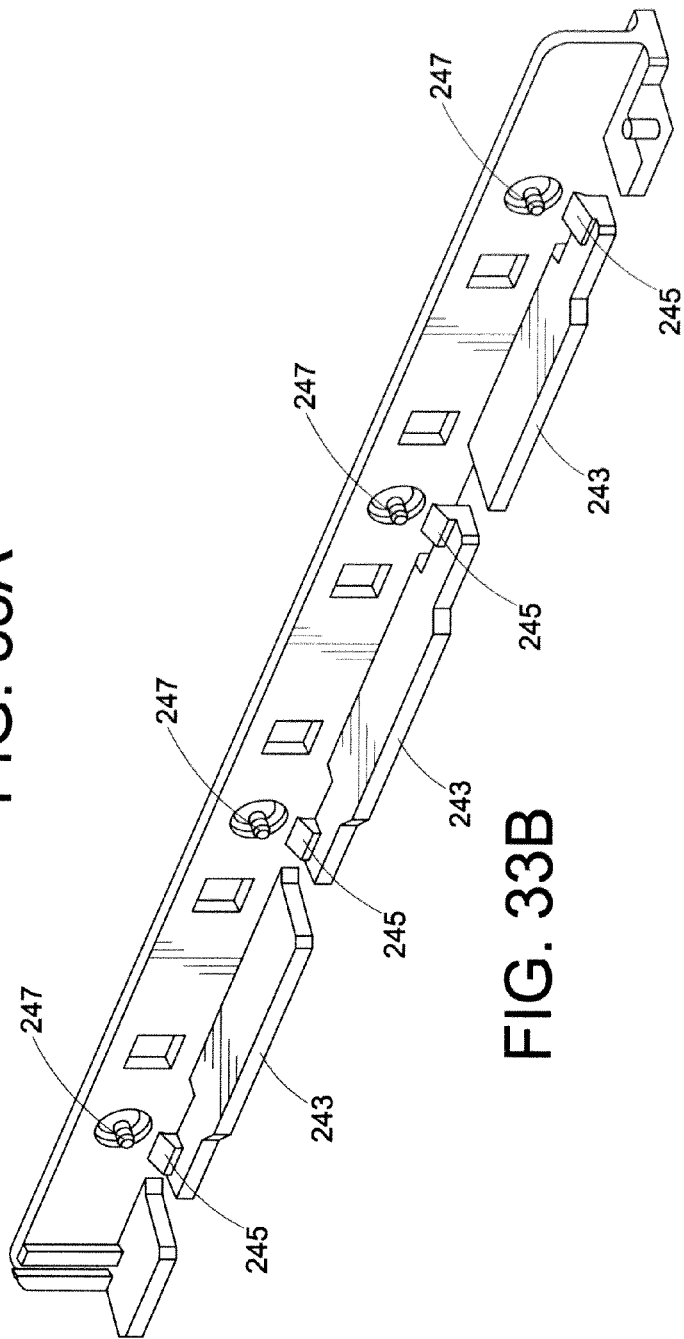

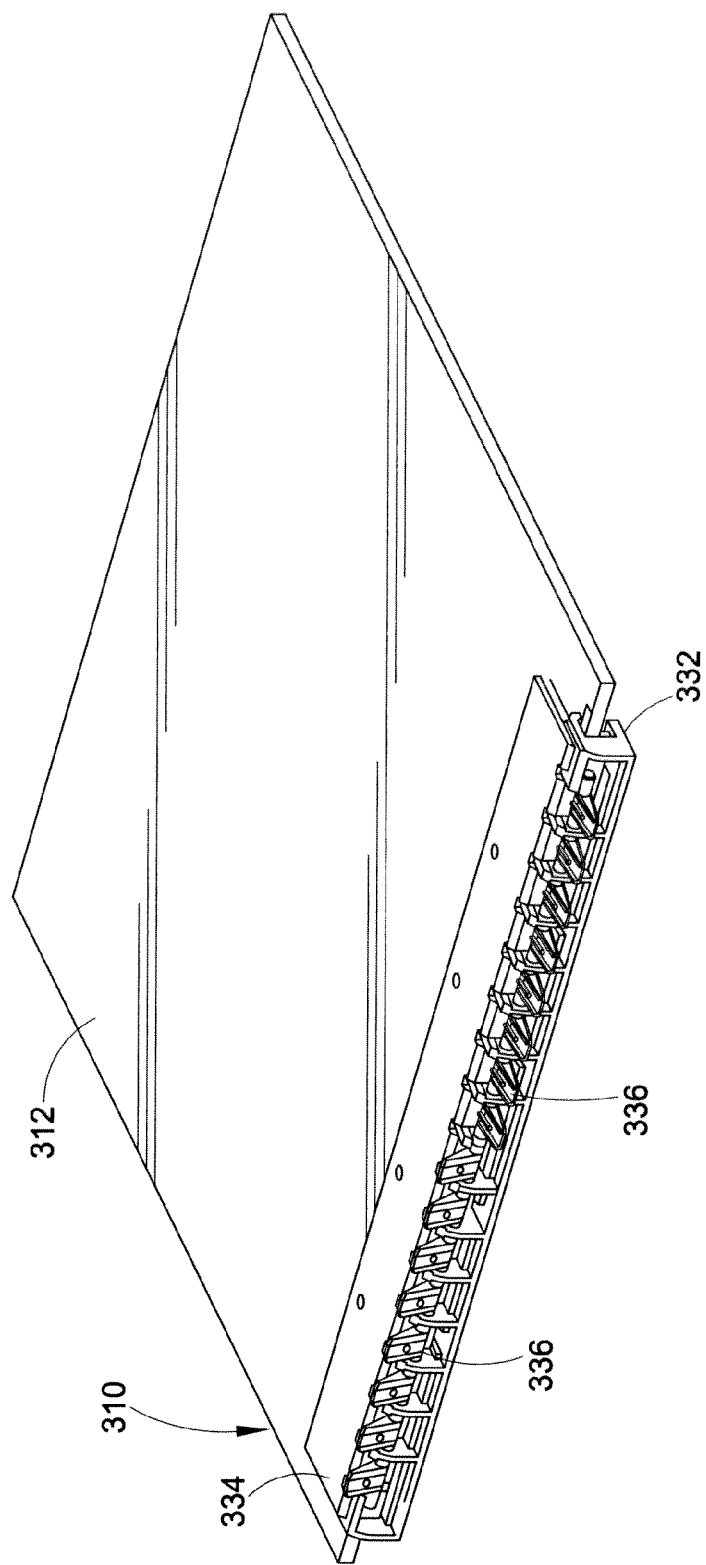

EDGE-ILLUMINATED FLAT PANEL AND LIGHT MODULE FOR SAME

This application claims the benefit of U.S. Provisional Ser. No. 61/453,299, filed Mar. 16, 2011, the disclosure of which is herein incorporated by reference.

BACKGROUND

The following relates to the illumination arts, lighting arts, solid state lighting arts, lamp and luminaire arts, illuminated flat panel arts, light engine arts, and related arts.

Backlights—the so-called edge coupled type—have historically employed a light source coupled to an edge of a light guiding plate (LGP), along which the light flux propagates by total internal reflection (TIR) with almost no losses. This enables constructing backlights with very large AR—typically of 50-100—for 10-20" diagonal LCDs used in existing portable and desktop computers. In these types of devices a light source, usually a cold cathode fluorescent lamp, introduces light into a light guiding plate (LGP), through an edge surface thereof. The LGP is so structured that part of the light entering through the edge radiates out through the LGP's front face.

Due to its inherent compactness, ease of operation and luminance efficiency, a much more suitable type of light source for such applications (instead of fluorescent lamps) is a light-emitting diode (LED). LEDs have also been used to illuminate signs, such as an exit sign, using edge lit technology. The present disclosure is directed to using edge lit technology for a general illumination lamp. However, it can have applicability in other edge lit environments

BRIEF DESCRIPTION

According to a first embodiment, an apparatus comprising a transparent or translucent panel and a light module comprising a plurality of light emitting diode (LED) devices is provided. The light module is mechanically connected to an edge of the panel with the LED devices oriented to inject light into the edge of the panel.

According to a further embodiment, a method for mechanically connecting a light module comprising LED devices to an edge of a transparent or translucent panel to form a unitary light source is provided. The connection is performed by at least two rotatable handles According to a third embodiment, a light engine module is provided. The module includes an elongated housing receiving a heat sink having a first planar portion and a second transverse position. An elongated printed circuit board hosting a plurality of high emitting diodes (LEDs) is received by the housing. At least two releasable locking elements urge the second portion of the heat sink into thermal communication with the printed circuit board.

BRIEF DESCRIPTION OF THE DRAWINGS

The following drawings, at least some of which are color drawings, are included with this Provisional application.

FIGS. 9 and 10 show diagrammatic side sectional views illustrating the unlocked and locked positions, respectively, of the locking bar of the LED based light module of the first embodiment.

FIG. 11 shows a sectional front view of the first embodiment.

FIG. 12 shows an enlarged sectional front view of a mating structure for aligning the LED based light module of the first embodiment and the mating edge of the flat panel of the first embodiment.

FIG. 17 shows a perspective view of the LED hoard of the LED based light module of the second embodiment.

FIGS. 18 and 19 show different perspective views of the structural support body of the LED based light module of the second embodiment.

FIGS. 31A and 31B show a diagrammatic side cross-section view illustrating the unlocked and locked positions of the third embodiment.

FIGS. 33A and 33B show front and rear view of the reflector of the third embodiment.

FIG. 35 shows a perspective view of the assembled fourth embodiment.

DETAILED DESCRIPTION

Figure 1:
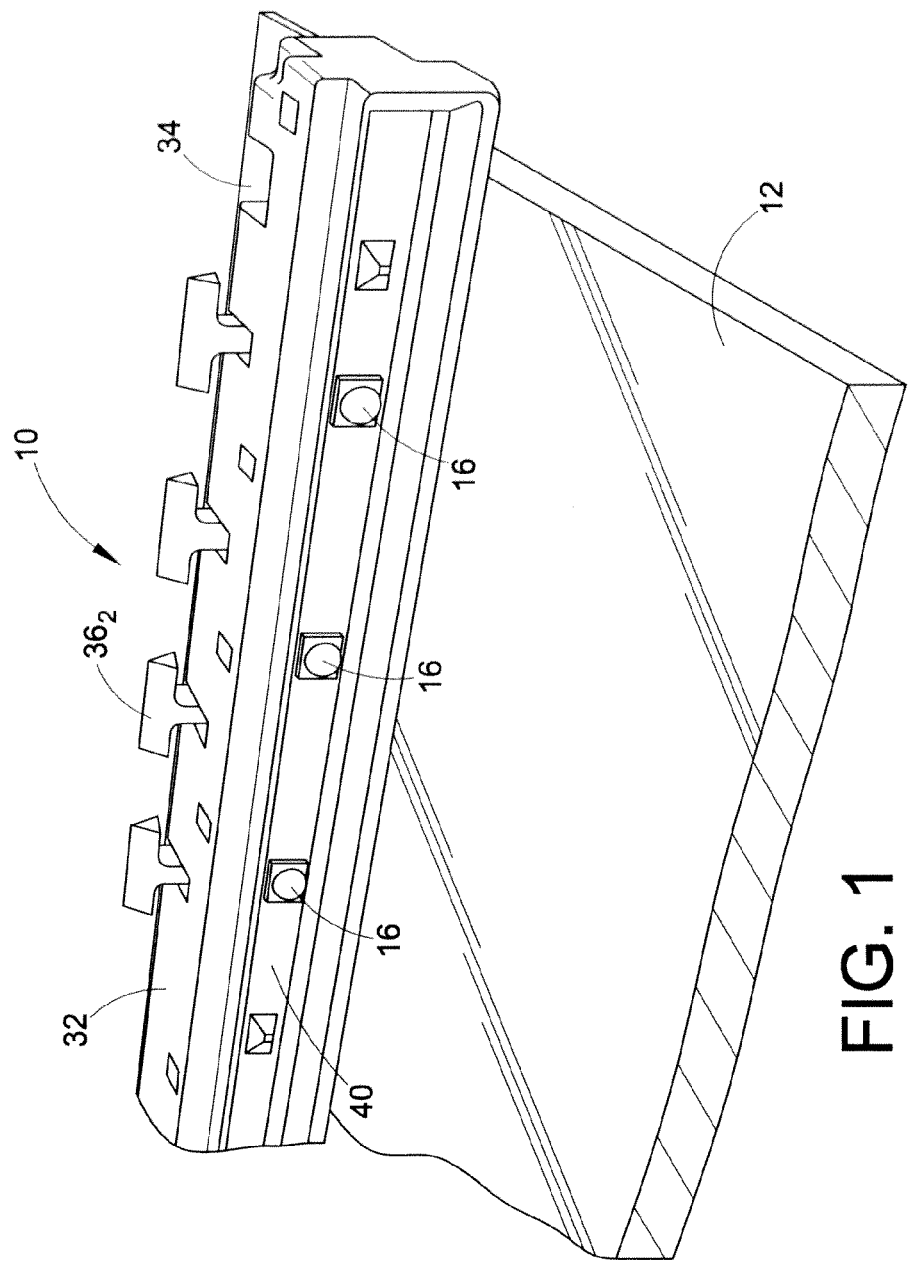
FIGS. 1 and 2 show perspective views of an illustrative first embodiment of a light source comprising a transparent or translucent flat panel and a removably mounted light emitting diode (LED) based light module providing edge injection of light into the flat panel.
Figure 2:
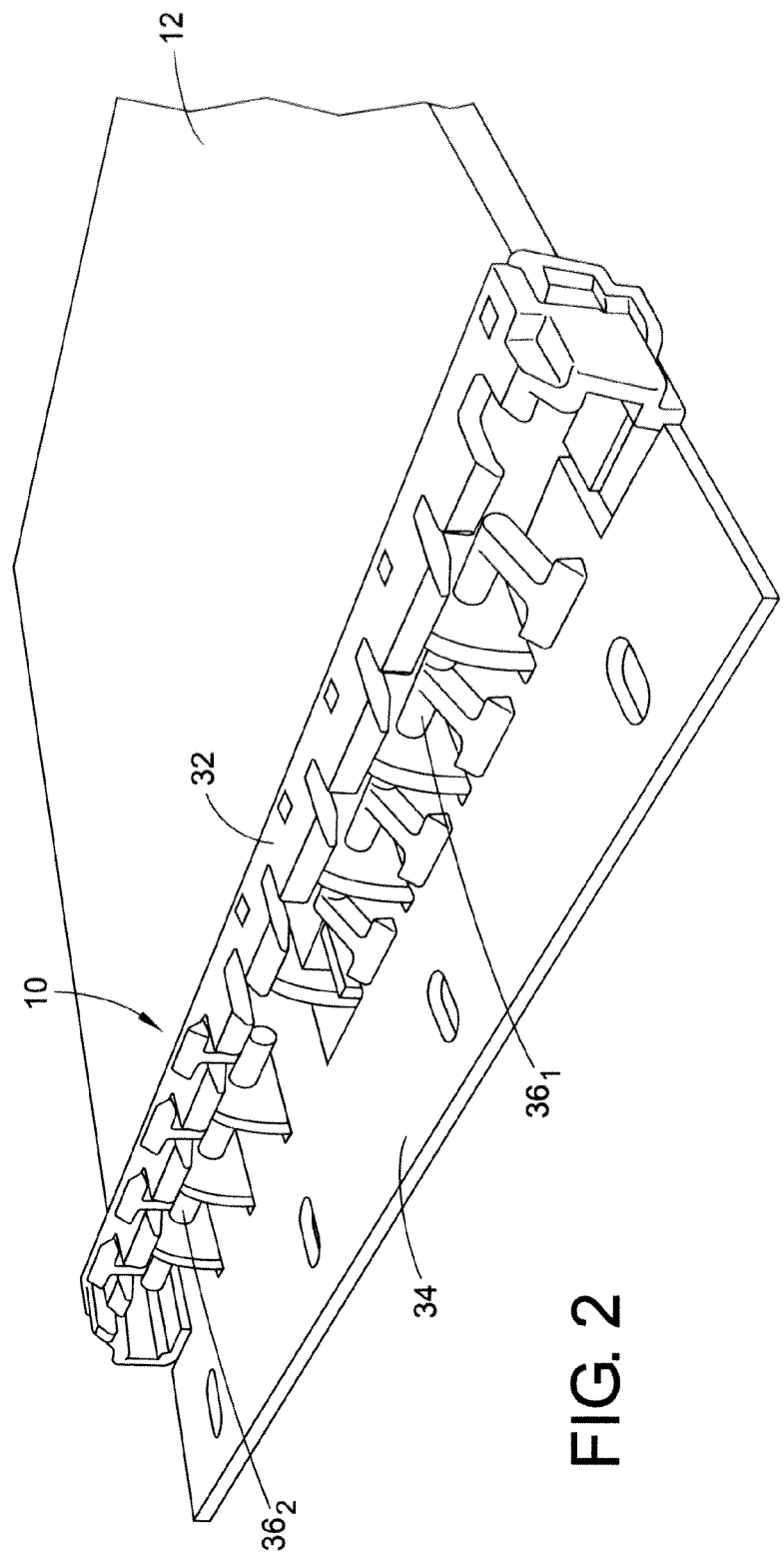
Figure 3:
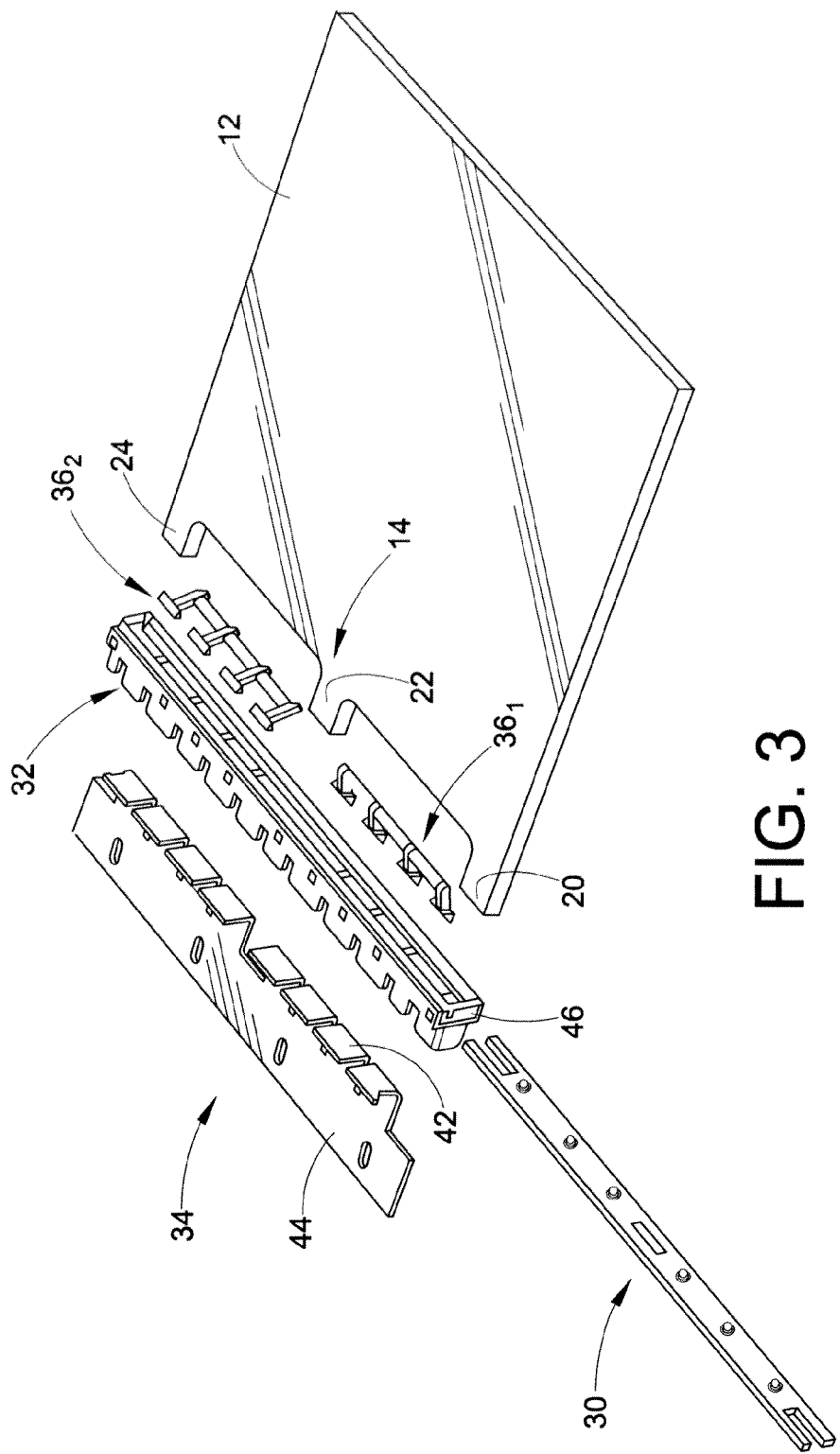
FIGS. 3 and 4 show perspective exploded views of the first embodiment.
Figure 4:
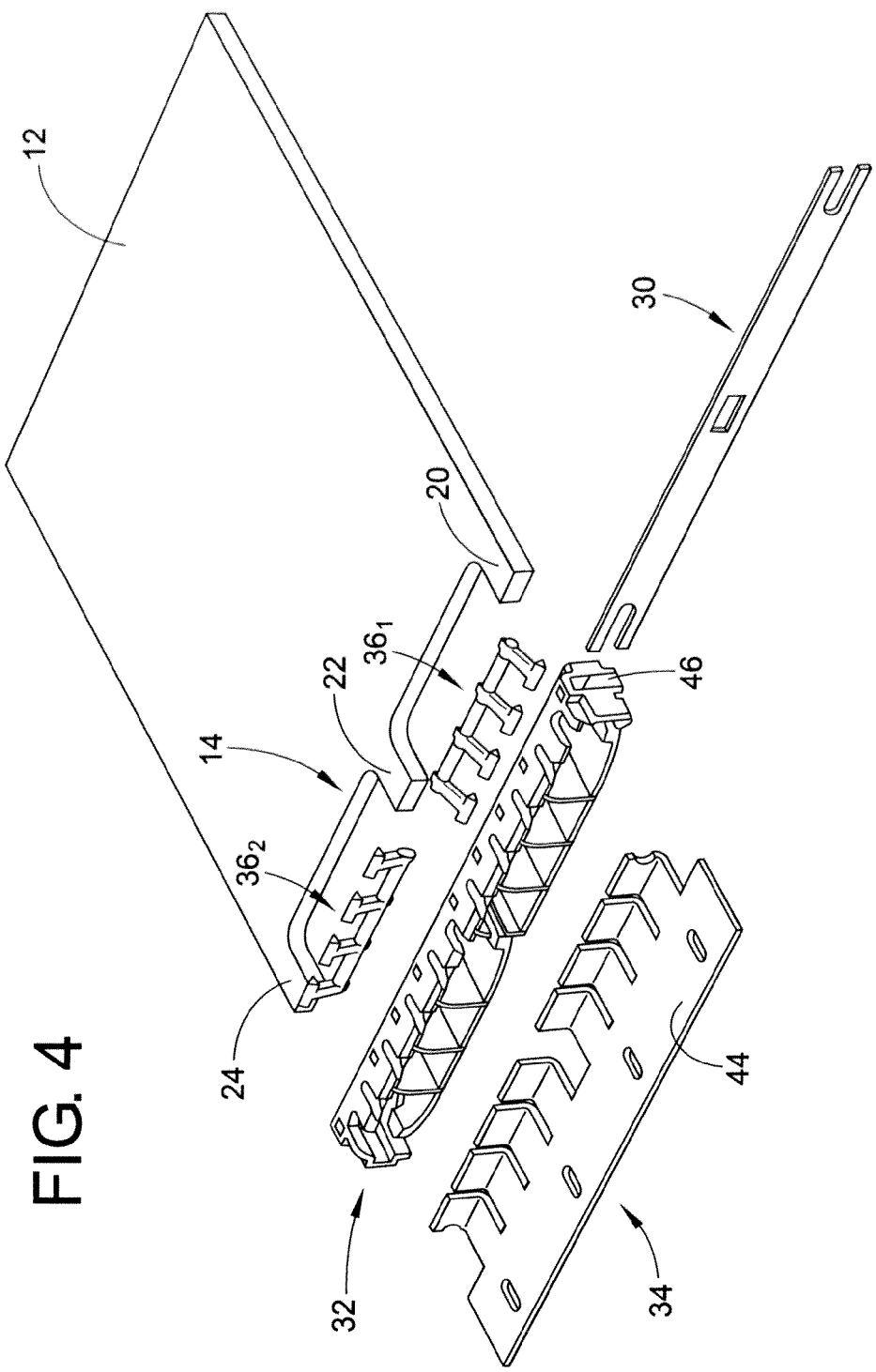
Figure 5:
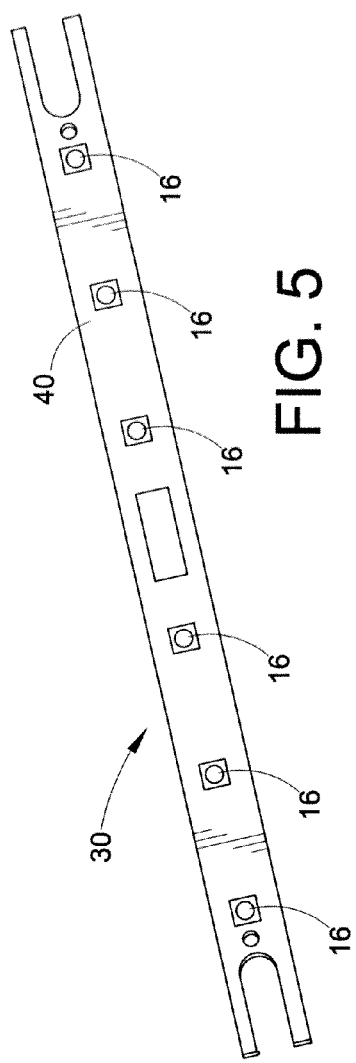
FIG. 5 shows a perspective view of the LED board of the LED based light module of the first embodiment.
Figure 6:
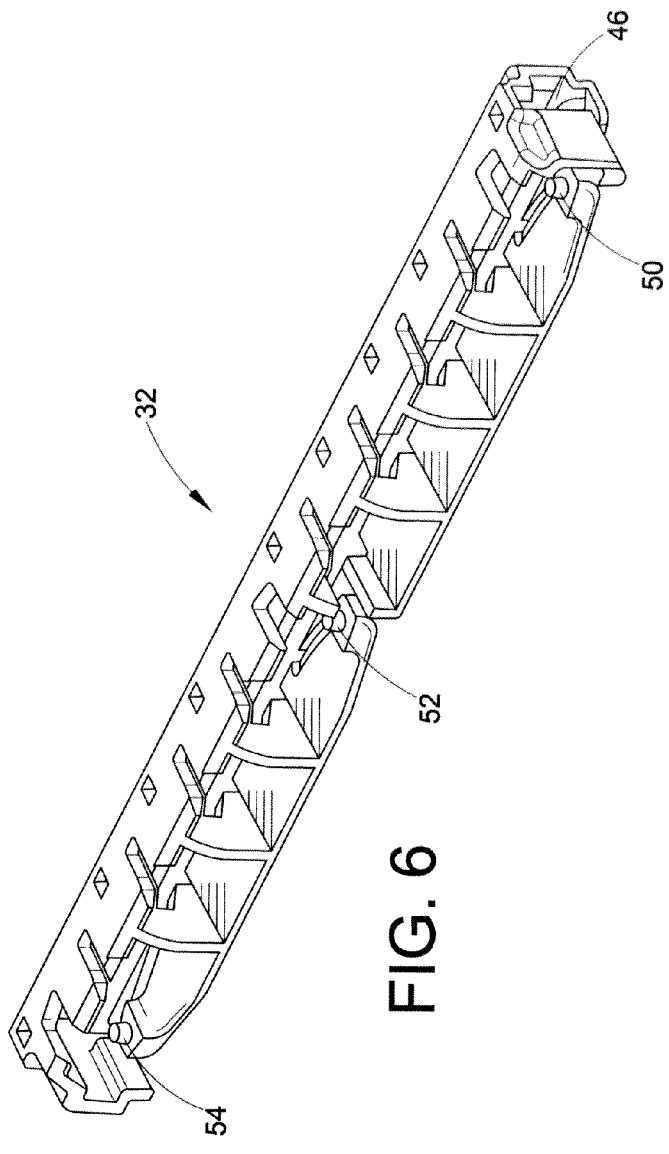
FIG. 6 shows a perspective view of the structural support body of the LED based light module of the first embodiment.
Figure 7:
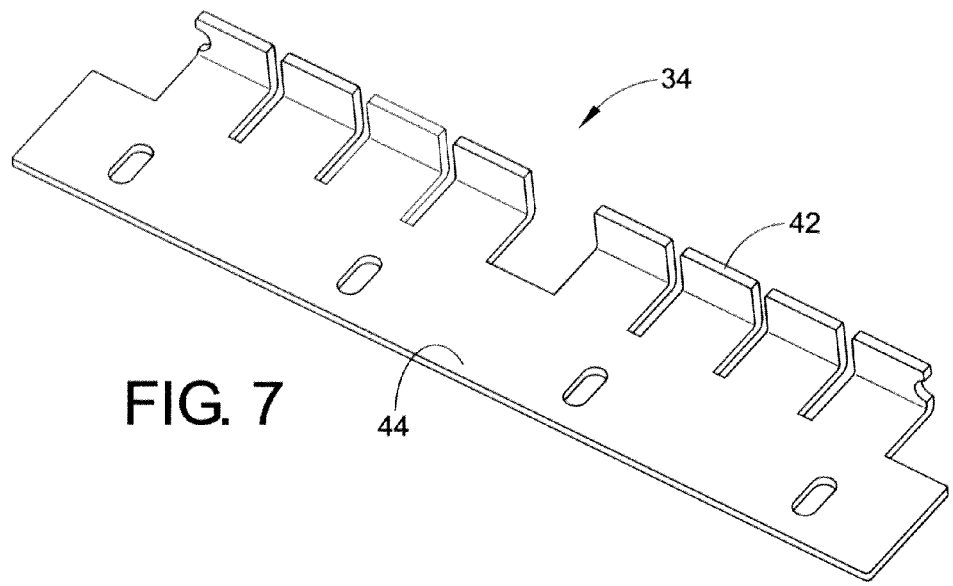
FIG. 7 shows a perspective view of the heat sink body of the LED based light module of the first embodiment.
Figure 8:
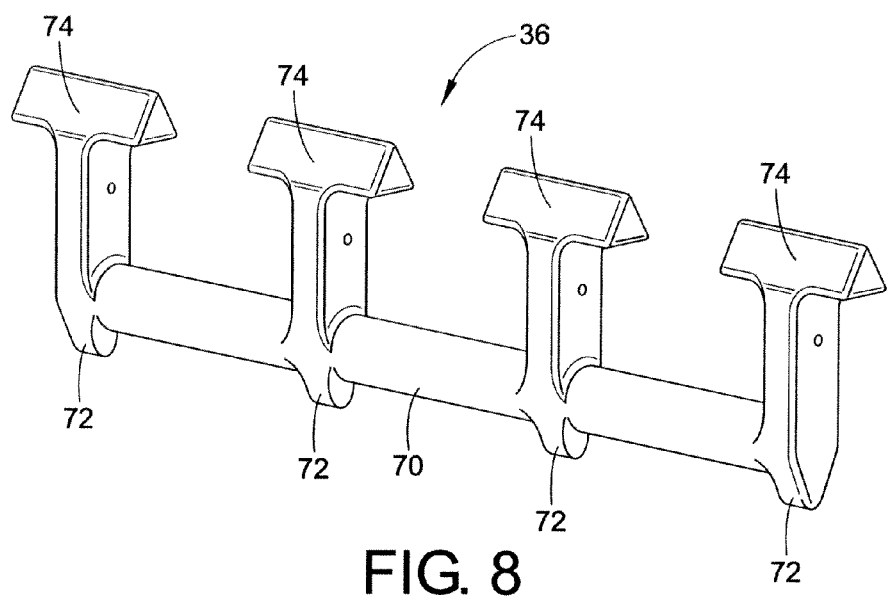
FIG. 8 shows a perspective view of a locking bar of the LED based light module of the first embodiment.
Figure 13:
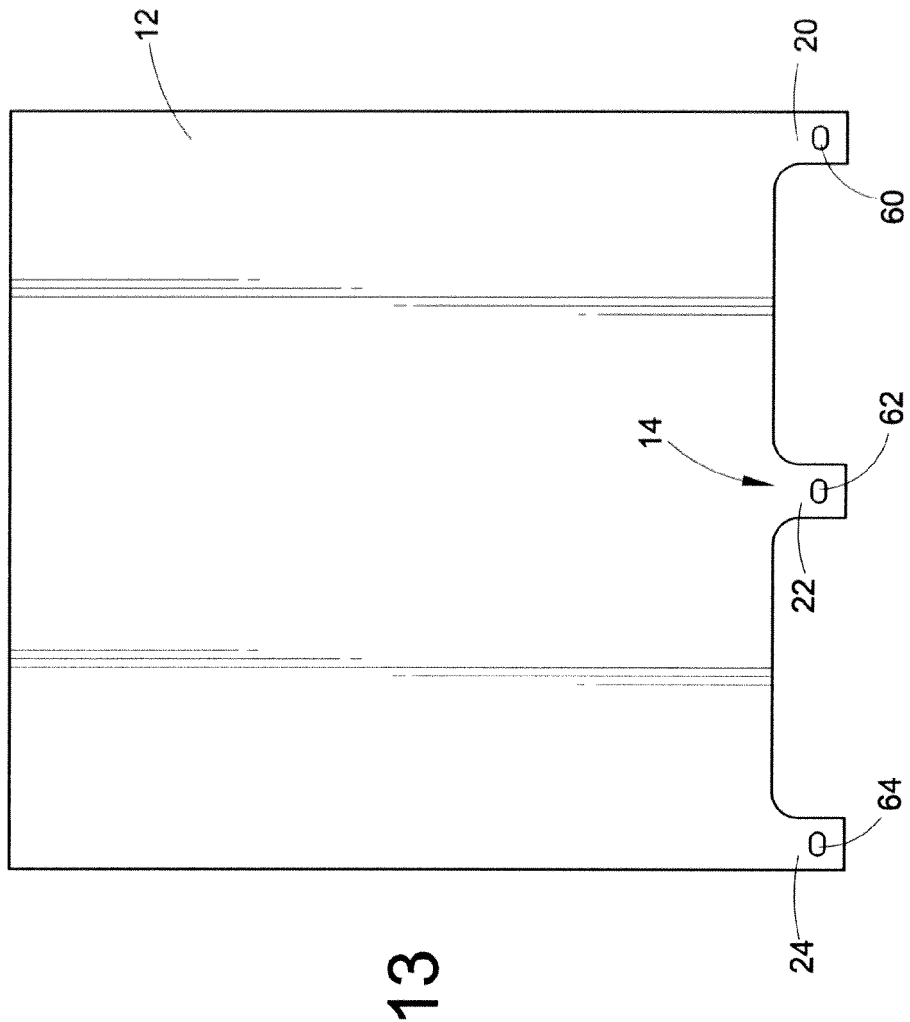
FIG. 13 shows a top plan view of the flat panel of the first embodiment illustrating features of the mating edge features for aligning the LED based light module of the first embodiment.

FIGS. 1-14 illustrate an illuminated panel comprising an LED-based light module 10 configured to mount at an edge of a transparent or translucent panel 12 in order to inject light into the panel 12. The transparent or translucent panel 12 has oppositely outwardly facing main sides connected by a perimeter edge. In some embodiments the transparent or translucent panel 12 is a waveguide or light guide that substantially retains or contains the edge-emitted light through total internal reflection (TIR). Optionally, such a waveguide or light guide may have suitable surface texturing on one or both main sides to cause the edge-injected and waveguide light to emit from one or both main surfaces. Such texturing can be designed to produce uniform planar illumination from the light-emitting main side or sides. For example, in a ceiling light application one side is designed to emit light, and the panel 12 is mounted in a ceiling fixture with the light-emitting main side facing downward. Alternatively, the texturing can be patterned to form lettering, a symbol, or some other design. The transparent or translucent panel 12 may optionally also include dispersed scattering particles, a wavelength-converting phosphor, or so forth. The term "transparent or translucent" applied to light of a wavelength of interest, and while visible light is typically contemplated, it is to be appreciated that in some embodiments the light may be in the ultraviolet or infrared range. For example, in some embodiments the panel 12 is made of a material that is transparent or translucent for ultraviolet light, and the light emitting main side or sides is coated with one or more phosphor materials selected to convert the ultraviolet light to a desired visible light such as white light.

The illustrative transparent or translucent panel 12 is a flat panel; however, it is contemplated for the panel to have some curvature. Such curvature can be formed in parallel in both main sides of the panel, for example to form a "bowed" panel. Alternatively, curvature can be formed in one main side while the other main side is flat. For example, the curved main side can be shaped to redirect waveguided light toward the flat side so as to enhance or otherwise affect light emission out of the flat side.

The LED-based light module 10 is designed to connect with a mating edge 14 of the transparent or translucent panel 12 in such a way that LED devices 16 of the LED-based light module 10 are positioned in a fixed (i.e., aligned) position respective to the edge 14 so as to emit light into the edge 14 and thereby inject light into the panel 12. The mating edge 14 of the panel 12 includes connecting features 20, 22, 24 for connecting the LED-based light module 10 with the edge 14 of the panel 12 in a precisely aligned fashion. The light module 10 is elongated with its elongation parallel with the mating edge 14 of the panel 12 when the light module 10 is connected with the edge 15, so that the light module 10 injects light along a substantial portion of the length of the edge 15 or injects light along the entire length of the edge 15.

The illustrative LED-based light module 10 includes four components: an LED board 30 supporting the LED devices 16; a structural support body 32; a heat sink body 34; and one or more locking bars 36 (namely two locking bars $36_1$, $36_2$ in the illustrative first embodiment).

The LED board 30 comprises a circuit board 40 supporting the LED devices 16. The circuit board 40 is elongated so that it can lie along the edge 14 of the panel 12 with the LED devices 16 distributed along the length of the edge 14 (or, equivalently, distributed along the length of the elongated circuit board 40) to provide a distribution of the light injected into the edge 14. In the illustrative LED board 30, the LED devices 16 are mounted to emit light in the general direction of away from the surface of the circuit board 40, and the circuit board 40 is oriented transverse to the plane of the panel 12.

It is alternatively contemplated to mount the LED devices to emit light in the general direction of parallel with the surface of the circuit board, and to orient the circuit board parallel with the plane of the panel, in which case the circuit board is suitably positioned slightly above or below the panel such that the LED devices are aligned with the edge of the panel into which the LED devices emit light. Some suitable LED devices emitting generally parallel with the mounting surface are edge emitting laser diodes and side-emitting LED packages.

As used herein, the term "LED device" is to be understood to encompass bare semiconductor chips of inorganic or organic LEDs, encapsulated semiconductor chips of inorganic or organic LEDs, LED chip "packages" in which the LED chip is mounted on one or more intermediate elements such as a sub-mount, a lead-frame, a surface mount support, or so forth, semiconductor chips of inorganic or organic LEDs that include a wavelength-converting phosphor coating with or without an encapsulant (for example, an ultra-violet or violet or blue LED chip coated with a yellow, white, amber, green, orange, red, or other phosphor designed to cooperatively produce white light), multi-chip inorganic or organic LED devices (for example, a white LED device including three LED chips emitting red, green, and blue, and possibly other colors of light, respectively, so as to collectively generate white light), or so forth. The LED devices 16 may be configured to collectively emit a white light beam, a yellowish light beam, red light beam, or a light beam of substantially any other color of interest for a given illuminated panel application. The LED devices 16 may be incoherent light emitters, or may be configured with a resonant cavity in order to provide stimulated emission (e.g., semiconductor laser diode light emitting devices).

The circuit board 40 supports the LED devices 16 and also provides printed circuitry (not shown) for electrically interconnecting the LED devices 16 in order to be powered by a suitable power source (not shown) connecting with the LED based light module 10 by a pigtail, electrical wires or cable terminating in an electrical connector, a plug designed to snap into a receptacle, or other suitable connection (not shown). While the use of the circuit board 40 provides a convenient package for the electrical wiring, it is also contemplated for the LED devices 16 to be mounted on a support that omits printed circuitry and to instead use chip-to-chip wire bonding or other suitable wiring to electrically interconnect the LED devices 16 on the support.

The structural support body 32 and the heat sink body 34 together define the housing or mechanical structure of the LED based light module 10. The heat sink body 34 comprises a thermally conductive material such as aluminum, copper, silver, or so forth, or a combination thereof. Alternatively, in some embodiments the heat sink body 34 may comprise a lightweight former such as a plastic former that is coated by a suitable thermally conductive material such as an electroplated copper layer. The heat sink body 34 is an elongated "L" shaped structure having two mutually transverse planar portions forming the a first "mounting" planar portion 42 on which the LED board 30 mounts, and a second "heat radiating" planar portion 44 generally transverse to the mounting portion 42 and extending outside of the LED based light module 10 to provide exposed surface area for heat to transfer into the air (or other ambient) by a combination of convection and radiation. Optionally, the interface or mating surfaces between the "backside" of the circuit board 40 (that is, the side of the circuit board 40 opposite the side on which the LED devices 16 are mounted) and the mounting planar portion 42 of the heat sink body 34 include thermally conductive layers or adhesive. For example, in some embodiments the circuit board 40 is a metal core printed circuit board (MCPCB) having a copper backside (the "metal core") that provides a thermally conductive interface with the mounting portion 42 of the heat sink body 34. Optionally, a the y conductive adhesive bonds the circuit board 40 to the heat sink body 34.

The "L" shaped heat sink body 34 with mutually transverse portions 42, 44 advantageously enables the heat radiating extension to be parallel with the transparent or translucent panel 12 (thus providing a low profile assembly) while orienting the LED board 30 orthogonal to the panel 12. In alternative embodiments in which the LED devices emit parallel with the circuit board, a planar heat sink body may be employed that omits the "L" bend. In this case the planar heat sink body is oriented parallel with the panel and parallel with the circuit board which rests on top of the planar heat sink body.

The structural support body 32 is shaped to assemble together with the heat sink body 34 to form the housing or main structure of the LED based light module 10, and to support the locking bars $36_1$, $36_2$ in pivoting fashion. In the illustrative first embodiment the structural support body 32 does not contribute to heat sinking of the LED devices 16 or to electrical powering of the LED devices 16. Accordingly, the structural support body 32 can be made of any mechanically sturdy material such as plastic, metal, or so forth.

The LED board 30 mounts into the housing 32, 34 via a slot 46 defined between the mounting portion 42 of the heat sink body 34 and an interior surface 48 of the structural support body 32. Once inserted into the slot 46, the LED board 30 is locked precisely into position by the locking bars 36 which compress the circuit board 40 between the interior surface 48 of the structural support body 32 and the mounting planar portion 42 of the heat sink body 34. For illustrative purposes, the locking bars $36_1$, $36_2$ are shown in FIGS. 1-4 and 11 with the locking bar $36_1$ in the locked position (also shown in FIG. 10) and the locking bar $36_2$ in the unlocked position (also shown in FIG. 9). With reference FIG. 8, each locking bar 36 includes a shaft 70 that mounts to the structural support body 32 in pivoting fashion, a set of cams 72, and one or more handles 74. FIG. 9 shows the unlocked position of the locking bar 36 (also shown as locking bar $36_2$ in FIGS. 1-4 and 11). In the unlocked position the handles 74 are oriented "up" (in the orientation of FIGS. 9 and 10) and the cams 72 are disengaged. To lock the LED module 30 into place in the slot 46, the handles 74 are rotated about the shaft 70 in the "lock" direction L shown in FIG. 9. This rotates the cams 72 to cam against the mounting planar portion 42 of the heat sink body 34, as seen in FIG. 10. This causes the cams 72 to press against the mounting planar portion 42 of the heat sink body 34, and simultaneously causes the shaft 70 to press in the opposite direction against the structural support body 32. The combined effect is to compress the circuit board 40 between the mounting planar portion 42 of the heat sink body 34 and the interior surface 48 of the structural support body 32.

The illustrative first embodiment employs two structural elements 32, 34 to form the housing or main structure of the LED based light module 10, and further employs the locking bars 36 to secure the circuit board inside the housing 32, 34. However, it is also contemplated to employ a single-piece housing, for example made by injection molding or the like. In such a case the single-piece housing is suitably made of metal or another thermally conductive material in order to provide the heat sink body, unless the LED devices are of sufficiently low power that a heat sink body is not necessary. Moreover, the illustrative locking bars 36 are optionally omitted if the LED board 30 is secured onto or inside the housing or support structure by another mechanism such as soldering.

As already noted, the mating edge 14 of the transparent or translucent panel 12 includes connecting features 20, 22, 24 for connecting the LED-based light module 10 with the edge 14 of the panel 12 in a precisely aligned fashion. Toward this end, the housing or main structure 32, 34 of the LED based light module 10 (and more particularly the structural support body 32 in the illustrative first embodiment) includes connecting features 50, 52, 54 corresponding to the respective connecting features 20, 22, 24 of the edge 14 of the panel 12. In the illustrative first embodiment the connecting features 20, 22, 24 of the edge 14 comprise tabs or protrusions that insert into the LED based light module 10, and the connecting features 50, 52, 54 of the LED based light module 10 include pins that mate with respective recesses or openings 60, 62, 64 (labeled only in FIG. 13) of the respective connecting features 20, 22, 24 of the edge 14 of the panel 12. The openings 60, 62 are slots while the opening 64 is a circular recess or a hole—this provides precise alignment while providing an additional degree of freedom (via the slots 60, 62) to facilitate ease of assembly. In this way, the LED based light module 10 snaps onto the edge 14 of the panel 12 and is frictionally held in place.

It is to be appreciated that the illustrative set of connecting features 20, 22, 24, 50. 52, 54, 60, 62, 64 is an illustrative example, and that substantially any set of connecting features providing the desired alignment can be used. As another illustrative variation, the pins can be located on the panel while the slots, holes, recesses, or the like are located on the LED based light module. Similarly, other quantities and types of mating features may be employed. Optionally, the connection can include a clamp or the like (not shown) for providing a secure connection.

The illustrative set of connecting features 20, 22, 24, 50, 52, 54, 60, 62, 64 is designed to align the LED based light module 10 and the edge 14 of the panel 12 both in the direction transverse to the edge 14 (and in the plane of the panel 12) and along the edge 14 (and again in the plane of the panel 12). The alignment in the direction transverse to the edge 14 is intended to ensure a predetermined spacing between the LED devices 16 and the edge 14, while the alignment along the edge 14 is intended to ensure the LED based light module 10 is "centered" along the edge 14.

In some other contemplated embodiments, precise alignment of the LED based light module along the plane of the panel 12 may be unnecessary for the application. In such embodiments, the "restrictiveness" of the connecting features may optionally be relaxed, for example by using long slots oriented parallel with the edge 14 as alignment features that precisely define the positioning in the direction transverse to the edge 14 (and thus fixes the LED device/edge spacing) without fixing light module position along the edge 14. An advantage of such a relaxed design is that a single LED based light module of length L could be replaced by two adjacently mounted light modules each of length L/2 (or, more generally, LED-based light modules of various lengths could be manufactured and combined as desired for particular applications).

The disclosed approach in which the LED based light module connects to the edge of the panel has substantial advantage. It ensures precise alignment between the LED devices 16 and the panel edge 15 into which they inject light. The assembly of the panel and the LED based light module (or plural light modules, for example four modules mounted on the four edges of a square panel) can be installed as a unit in a ceiling light fixture, as a backlight for a liquid crystal device (LCD) display panel used in a television, computer display or the like, or other support that provides electrical power.

Figure 14:
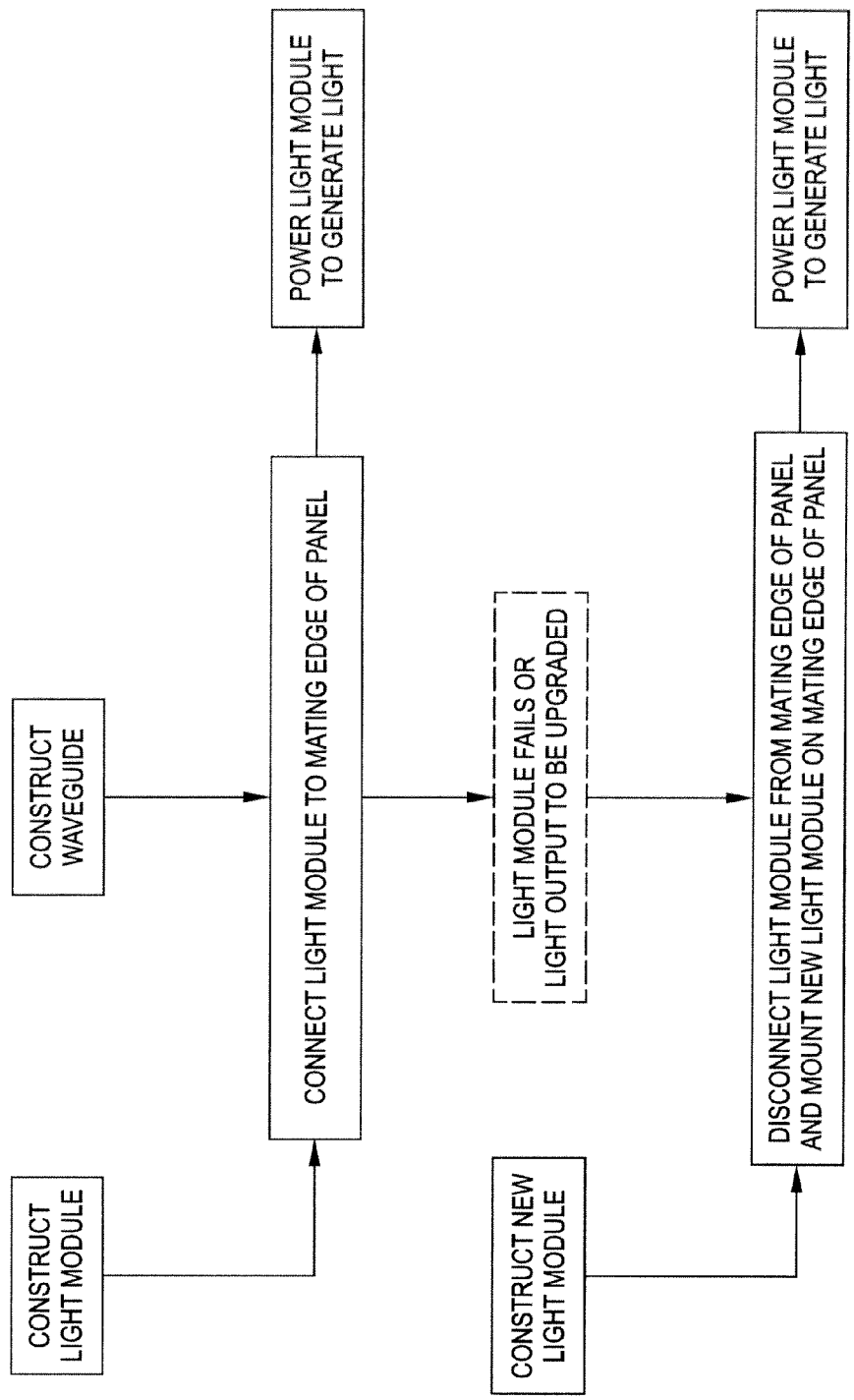
FIG. 14 diagrammatically shows an installation and maintenance/upgrade sequence suitably performed using the embodiment of FIGS. 1-14.

With reference to FIG. 14, some further advantages of the disclosed approach are set forth. The constructed light module is connected to the edge of the panel and the light module is energized to generate light. Subsequently, if the light module fails, it can be disconnected and a new light module connected and energized to generate light, thus enabling field maintenance of the panel light. In similar fashion, if subsequently the light requirements change, for example, due to a desire for white light of a different color temperature, color rendering index (CRI), or so forth, then the old light module can be disconnected and replaced by a new light module providing the desired light characteristics.

With reference to FIGS. 16-28, a second illustrative embodiment of a light source comprises a light emitting diode (LED) based light module 110 removably mechanically connecting to a side of a transparent or translucent flat panel 112 to provide edge injection of light into the flat panel 112. The light module 110 is mounted to inject light into an edge 114 of the flat panel 112. Again, although the illustrative panel 112 is a flat panel, it is also contemplated for the panel to have some curvature of one or both main sides, various waveguiding characteristics optionally including texturing of one or both main sides to control light output, and so forth as described herein with reference to the panel 12 of the first embodiment. The light module 110 includes LED devices 116, which are analogous to the LED devices 16 of the first embodiment.

The LED based light module 110 includes four components: an LED hoard 130 supporting the LED devices 116; a structural support body 132; a heat sink body 134; and a plurality of locking levers 136, 136'.

The LED hoard 130 comprises a circuit board 140 supporting the LED devices 116. The circuit board 140 is elongated so that it can lie along the edge 114 of the panel 112 with the LED devices 116 distributed along the length of the edge 14 (or, equivalently, distributed along the length of the elongated circuit board 140) to provide a distribution of the light injected into the edge 114. In the illustrative LED board 130, the LED devices 116 are mounted to emit light in the general direction of away from the surface of the circuit board 140, and the circuit board 140 is oriented transverse to the plane of the panel 112. As previously noted with reference to the first embodiment, in an alternative embodiment the circuit board can be parallel with the panel and the LED devices can be edge emitting laser diodes, side-emitting LED packages, or the like. The circuit board 140 supports the LED devices 116 and also provides printed circuitry (not shown) for electrically interconnecting the LED devices 116 in order to be powered by a suitable power source (not shown) connecting with the LED based light module 110 by a pigtail, electrical wires or cable terminating in an electrical connector, a plug designed to snap into a receptacle, or other suitable connection (not shown). While the use of the circuit board 140 provides a convenient package for the electrical wiring, it is also contemplated for the LED devices 116 to be mounted on a support that omits printed circuitry and to instead use chip-to-chip wire bonding or other suitable wiring to electrically interconnect the LED devices 116 on the support.

The structural support body 132 and the heat sink body 134 together define the housing or mechanical structure of the LED based light module 110. The heat sink body 134 comprises a thermally conductive material such as aluminum, copper, silver, or so forth, or a combination thereof Alternatively, in some embodiments the heat sink body 134 may comprise a lightweight former such as a plastic former that is coated by a suitable thermally conductive material such as an electroplated copper layer. The heat sink body 134 has a generally "C" shaped cross-section defining a cavity that receives the LED module 130 and a portion of the structural support body 132. The LED module 130 mounts inside the recess defined by the "C" shaped cross-section of the heat sink body 134 with the backside of the circuit hoard 140 contacting the heat sink body 134. As with the first embodiment, thermal conductivity of this interface may be enhanced by making the circuit board 140 a metal core printed circuit board (MCPCB), and/or by using a thermally conductive adhesive, or so forth. The assembly of the heat sink body 134, LED module 130, and structural support body 132 is suitably secured together using screws, rivets, or other fasteners securing via illustrated mutually angled fastener openings of the respective components 134, 130, 132. Additionally or alternatively, other fastening approaches such as adhesives, soldering, clamps, or so forth may be employed. The structural support body 132 includes openings aligned with the LED devices 116 to allow the LED devices 116 to emit light toward the panel edge 114. In some embodiments, the openings may include reflector cups (not shown) to enhance the light injection into the panel edge 114.

In alternative embodiments, it is contemplated to integrate the heat sink body 134 and the structural support body 132 to form a unitary housing, that is preferably made of aluminum, copper, or another thermally conductive material. An advantage of the illustrative second embodiment in which the heat sink body 134 is separate from the structural support body 132 is that the heat sink body 134 does not provide substantial structural support and hence can be made of a material such as copper that is relatively flexible (and hence not an especially good structural material) and highly thermally conductive, while the structural support body 132 can be made of a suitable plastic or other material that is selected for its structural characteristics.

Figure 15:
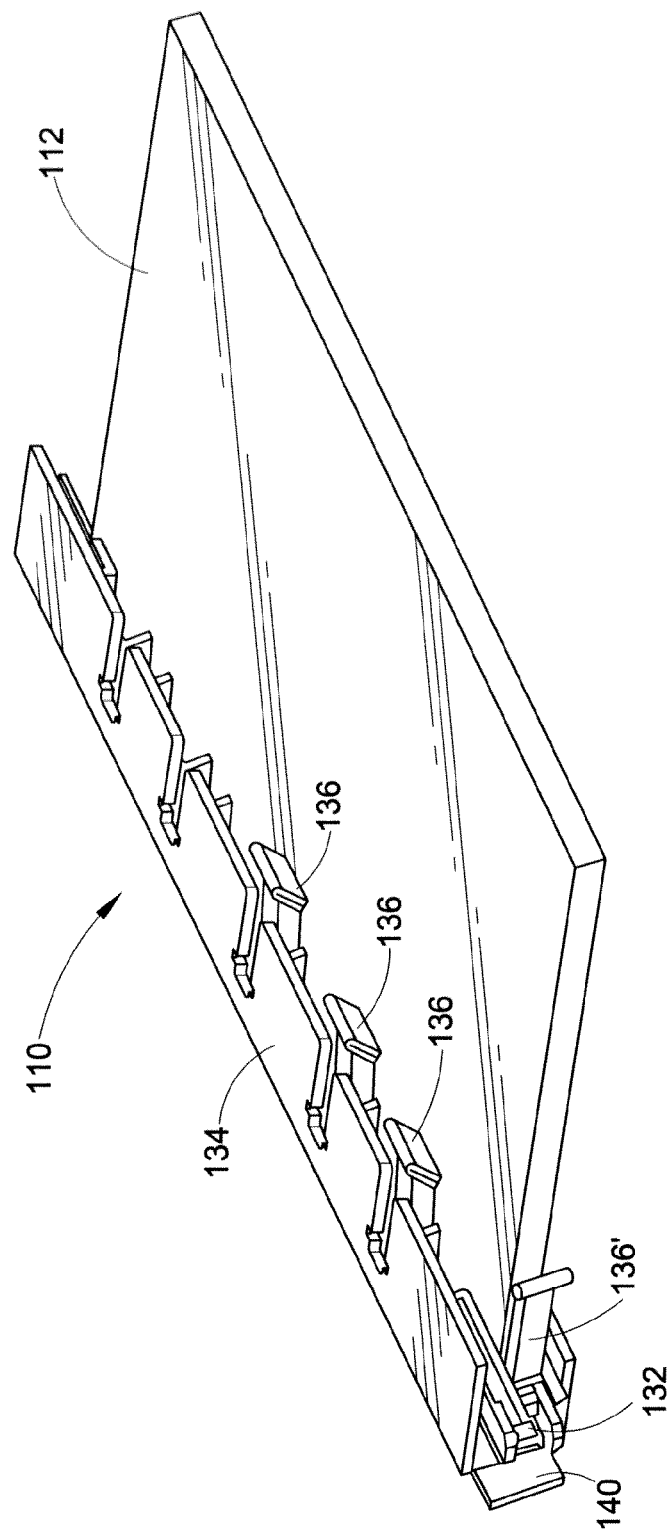
FIG. 15 shows a perspective view of a second illustrative embodiment of a light source comprising a transparent or translucent flat panel and a removably mounted light emitting diode (LED) based light module providing edge injection of light into the flat panel.
Figure 16:
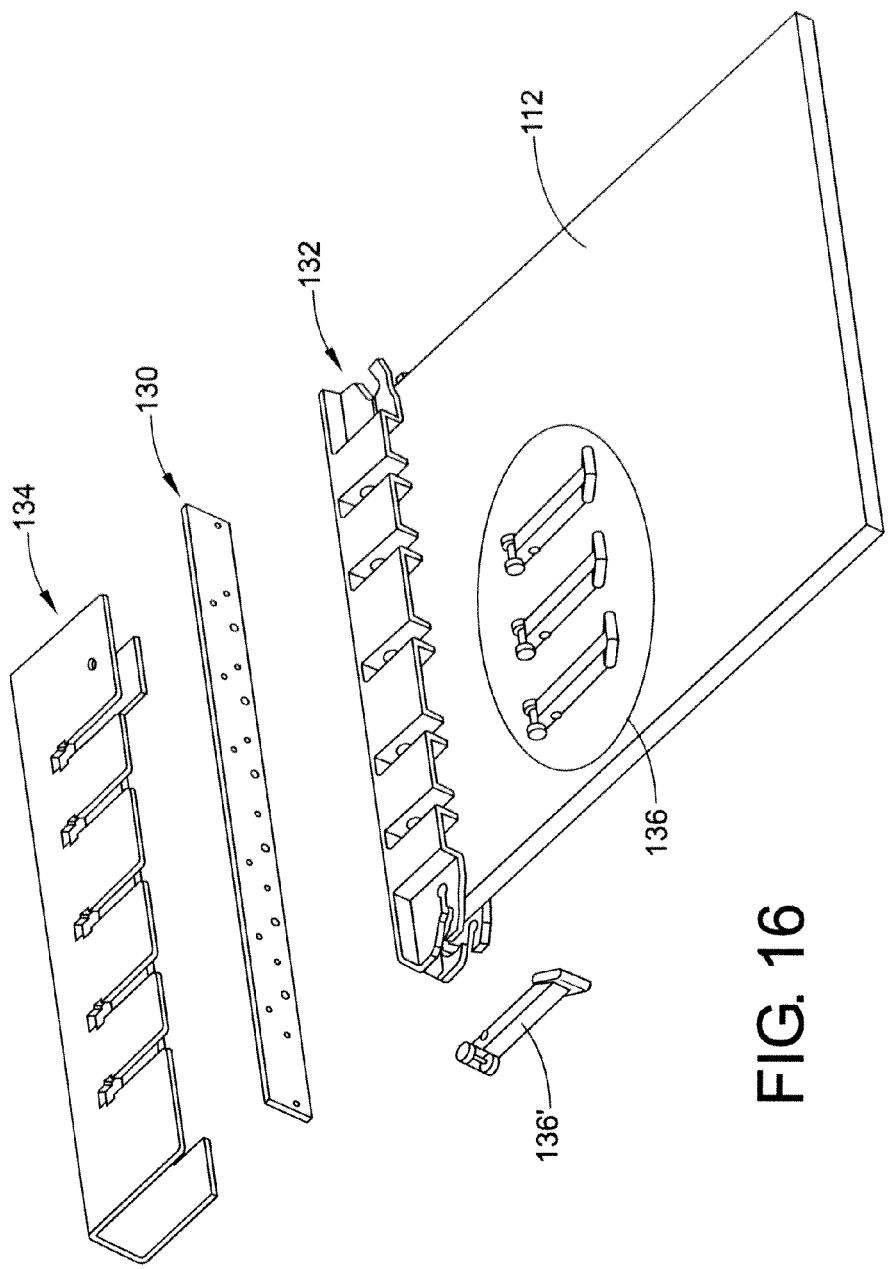
FIG. 16 shows a perspective exploded view of the second embodiment.
Figure 19:
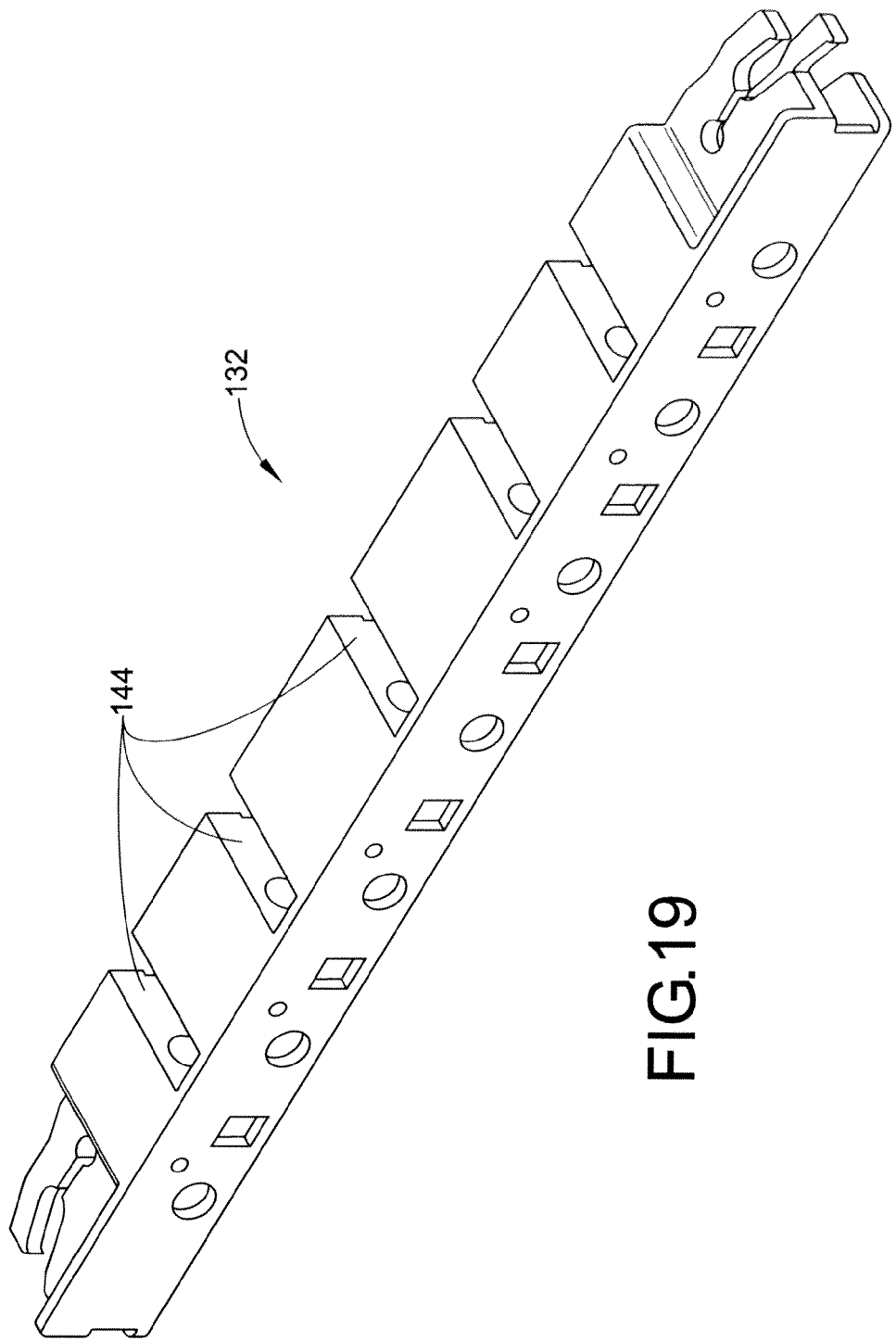
Figure 20:
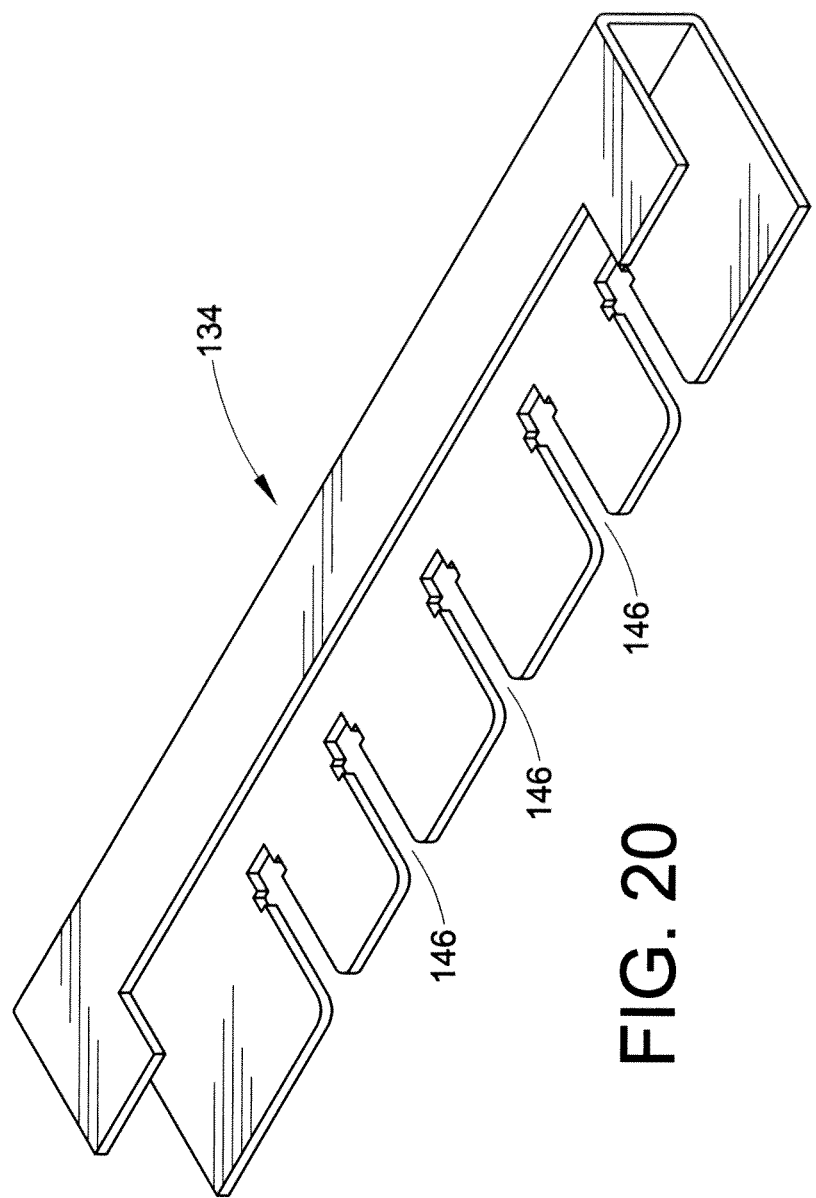
FIG. 20 shows a perspective view of the heat sink body of the LED based light module of the second embodiment.
Figure 21:
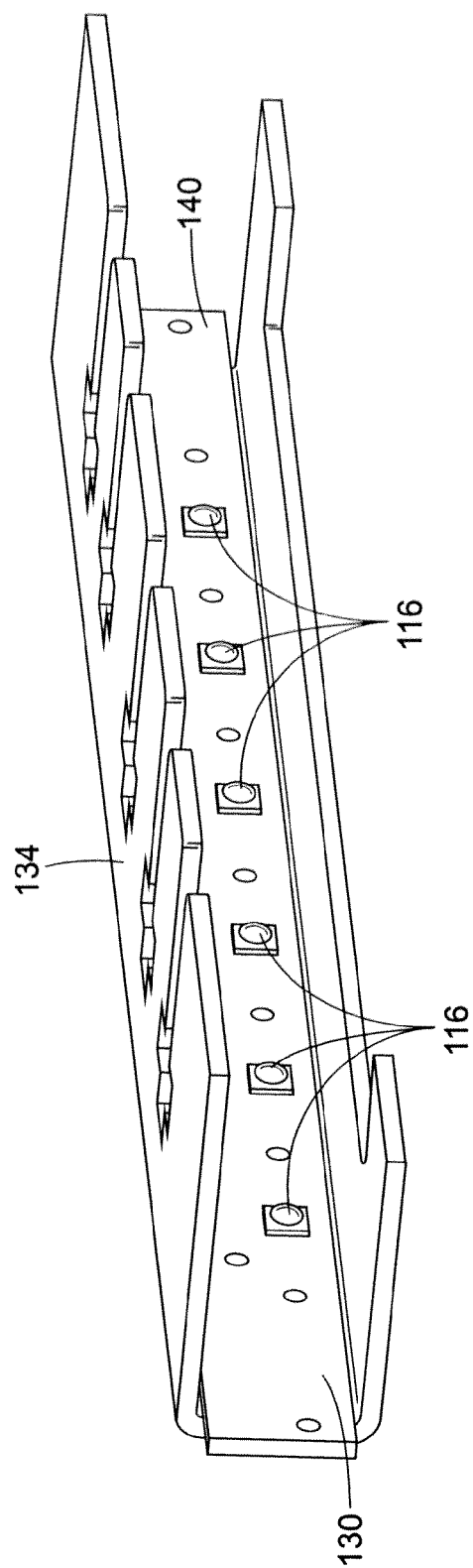
FIG. 21 shows a perspective view of the assembly of the LED board and the heat sink body.
Figure 22:
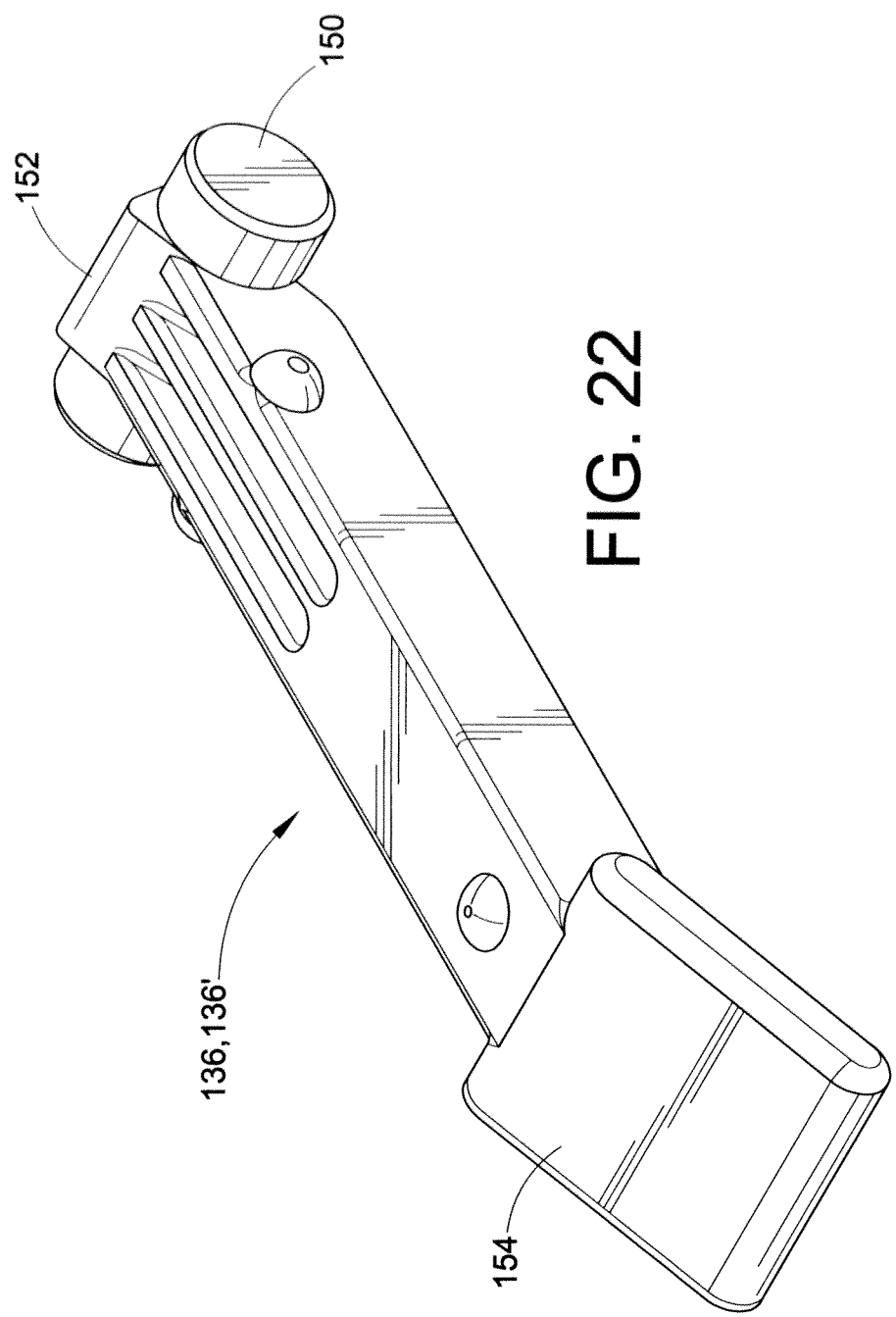
FIG. 22 shows a perspective view of one of the locking levers of the LED based light module of the second embodiment.
Figure 26:
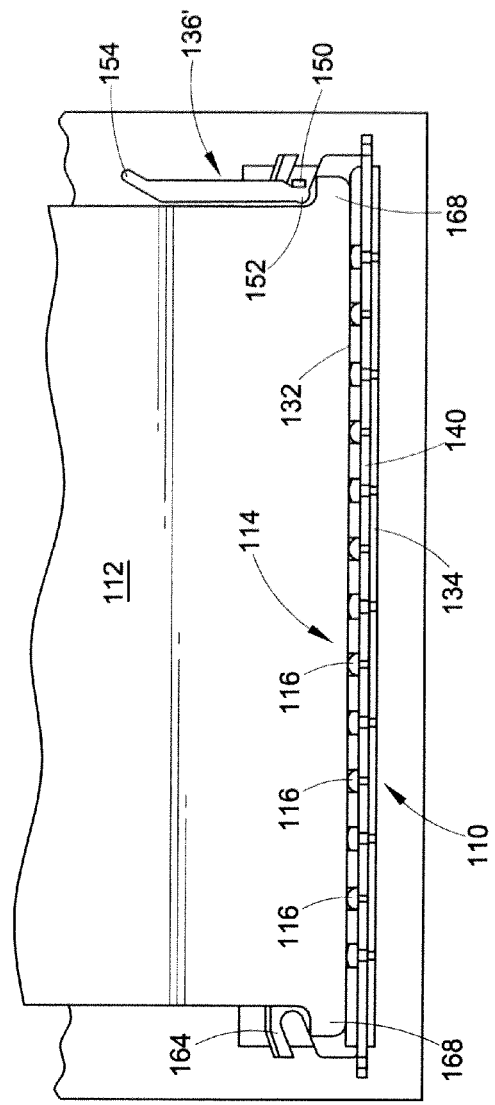
FIG. 26 shows a top sectional view of the assembly of the LED based light module and panel showing the edge locking levers that lock onto edges of the panel, with one edge locking lever omitted to reveal the corresponding mounting structure of the structural support body.

The locking levers 136, 136' are used to lock the connection of the LED based light module 110 to the edge 114 of the panel 112. (Note that this differs from the locking bars 36 of the first embodiment, which serve to lock the circuit board 40 between the mounting planar portion 42 of the heat sink body 34 and the interior surface 48 of the structural support body 132. The locking levers 136, 136' of the second embodiment are functionally analogous to the connecting features 20, 22, 24, 50, 52, 54, 60, 62, 64 of the first embodiment insofar as the locking levers 136, 136' contribute to securing the LED module 110 to the edge 114 of the panel 112). To accommodate the locking levers 136, the structural support body 132 includes slots 144 and the heat sink body 134 includes slots 146. Each locking lever 136, 136' includes a shaft 150 that mates into holes of the structural support body 132 in order to allow the locking lever to pivot about the shaft 150. The locking lever 136, 136' further includes a locking cam 152 and a handle 154, with the handle 154 located substantially further away from the pivot 150 as compared with the locking cam 152 in order to provide force multiplication. It should be noted that in illustrative FIGS. 15 and 16 some locking levers 136 are omitted to reveal corresponding mating aspects of the housing or mechanical structure 132, 134. In the illustrative second embodiment, most of the locking levers 136 are arranged to engage a main side of the panel 112; however, two locking levers 136' are "edge locking" levers arranged to engage edges of the panel 112 on either side of (and transverse to) the edge 114 into which the light module 110 injects light. In FIGS. 15, 16, and 26, one of the two edge locking levers 136' is omitted to reveal corresponding mating aspects of the housing or mechanical structure 132, 134.

Figure 23:
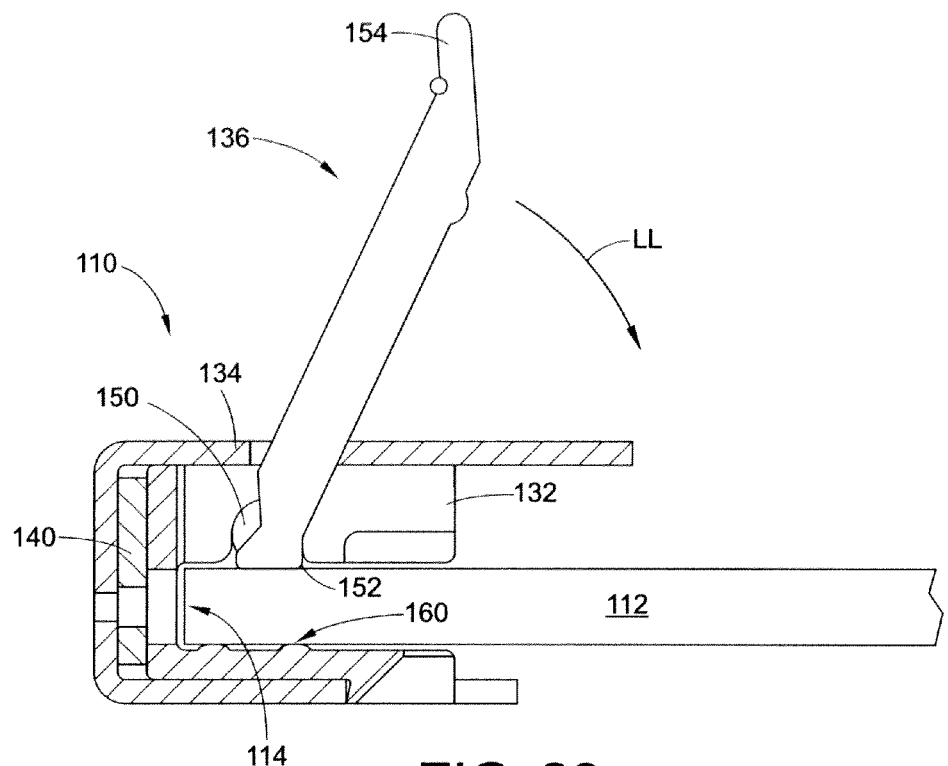
FIGS. 23 and 24 show unlocked and locked positions, respectively, of one of the locking levers locking onto on a main side of the panel.
Figure 24:
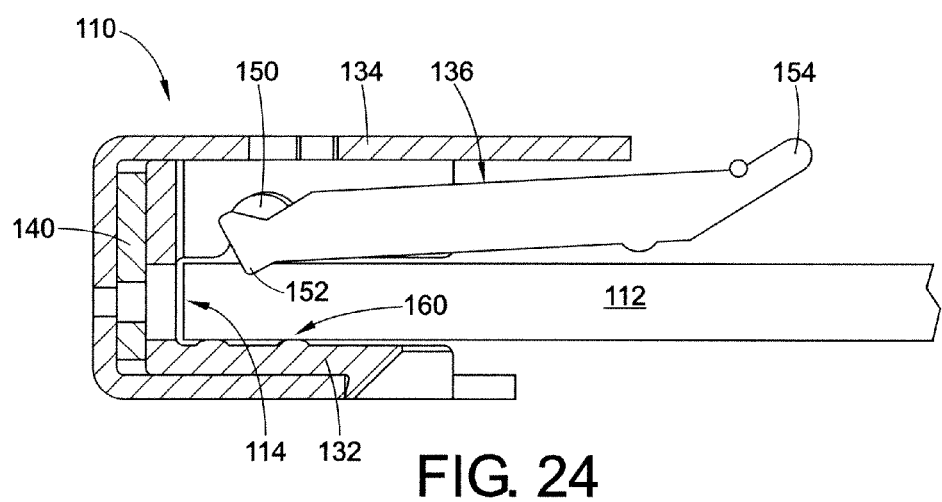
Figure 25:
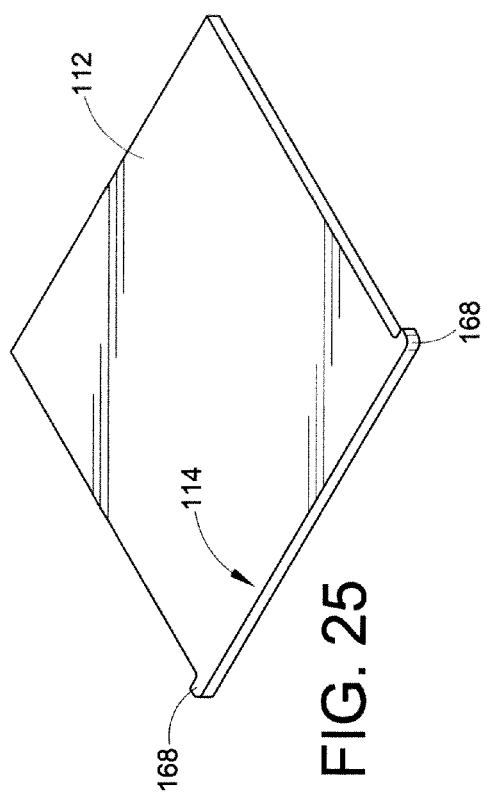
FIG. 25 shows a perspective view of the transparent or translucent panel of the second embodiment.

With reference to FIGS. 23 and 24, operation of one of the locking levers 136 that engages the main side of the panel 112 is illustrated. FIG. 23 shows the unlocked position of the lever 136. The locking cam 154 is seen to be disengaged from the proximate main side of the panel 112, and the handle 154 is raised. By moving the handle downward in the direction LL indicated in FIG. 23, the lever 136 is moved into its locked position shown in FIG. 24. In the locked position, the locking cam 154 presses against the proximate main side of the panel 112 to compress the edge 114 of the panel 112 between the locking cam 154 and an interior surface 160 of the structural support body 132.

In the second embodiment, the separation between the LED devices 116 and the edge 114 of the panel 112 (in other words, the alignment of the LED based light module 110 and the edge 114 of the panel 112 both in the direction transverse to the edge 114 and in the plane of the panel 112) is fixed by inserting the edge 114 of the panel 112 into the structural support body 132 until the edge 114 contacts a stopping surface of the structural support body 132.

Figure 27:
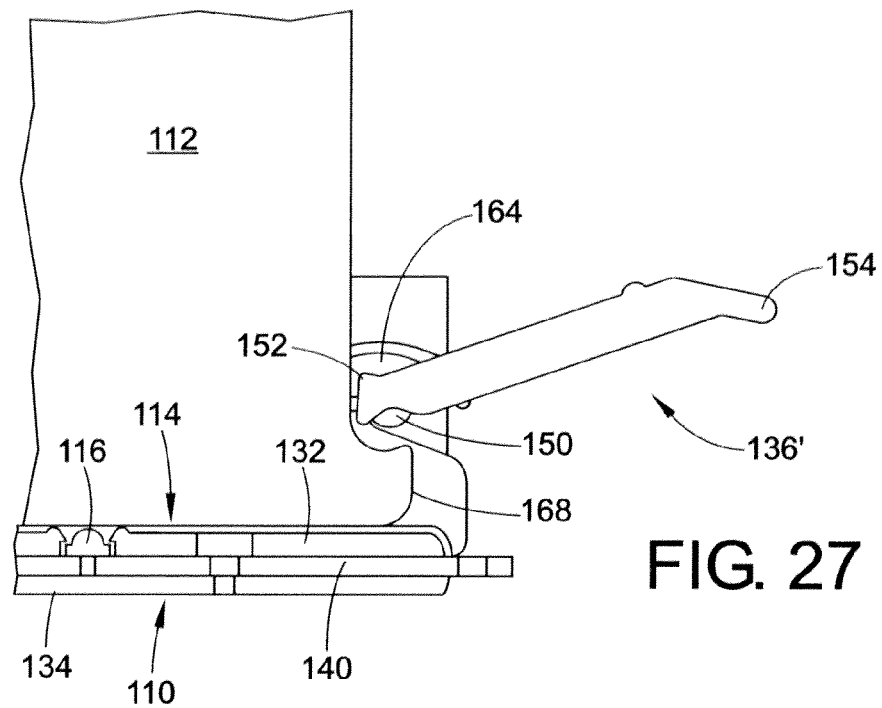
FIGS. 27 and 28 show unlocked and locked positions, respectively, of one of the edge locking levers locking onto on an edge of the panel.
Figure 28:
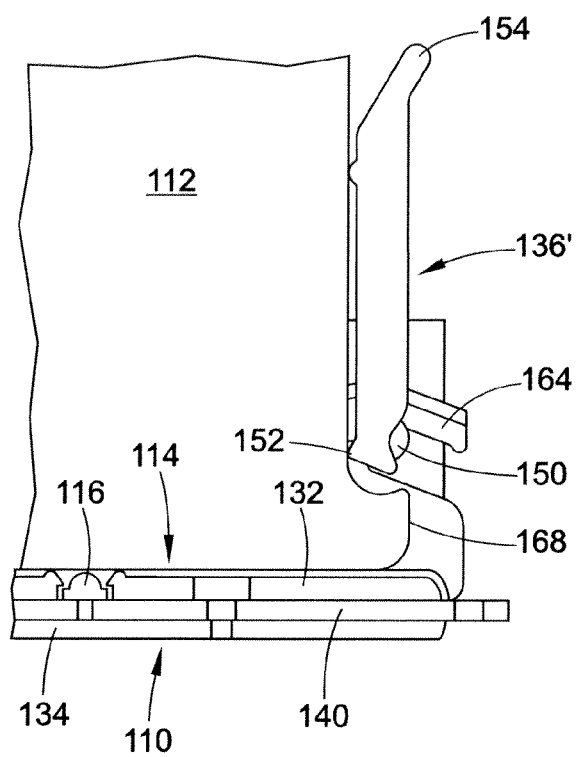
Figure 29:
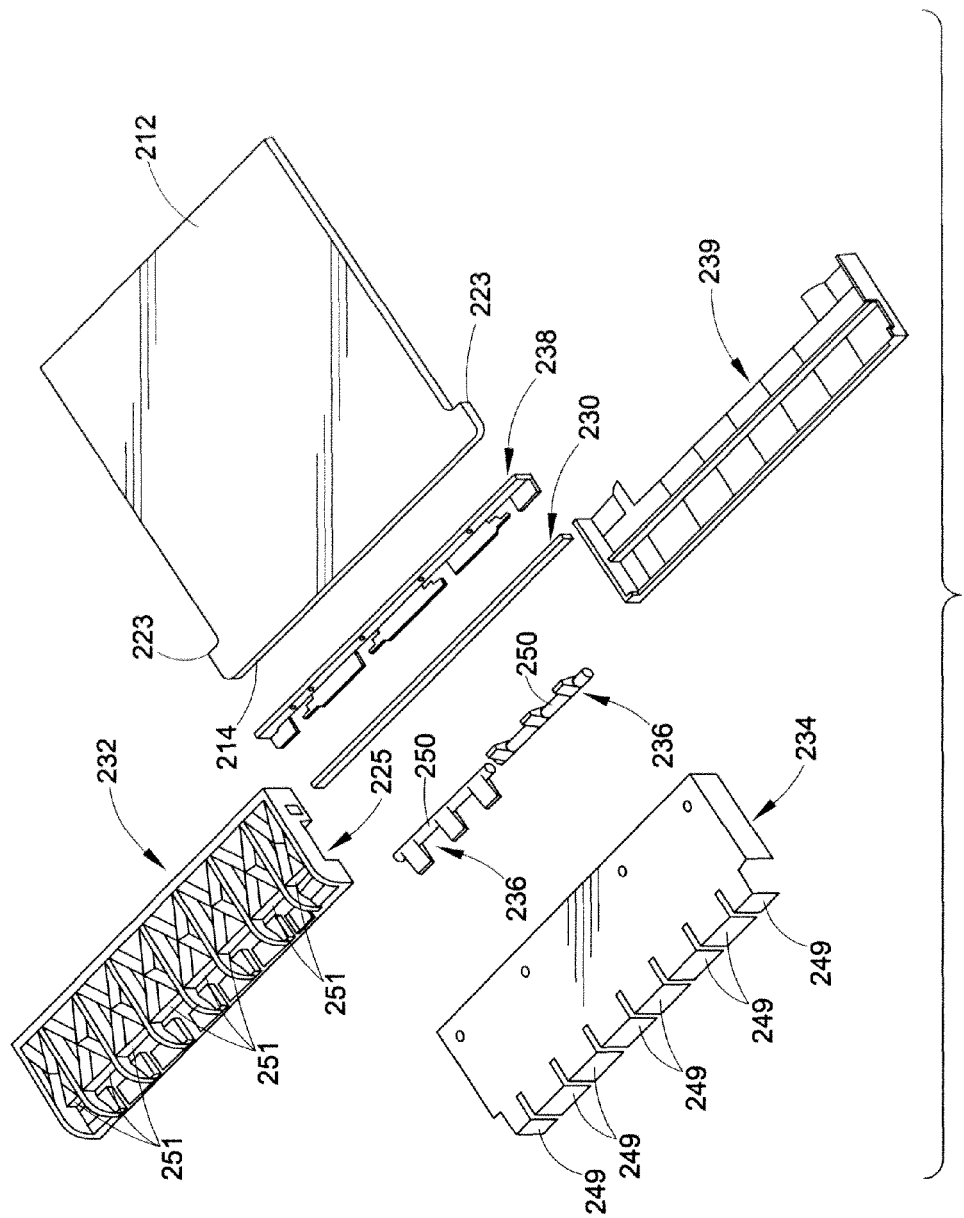
FIG. 29 shows a perspective exploded view of a third embodiment.
Figure 30:
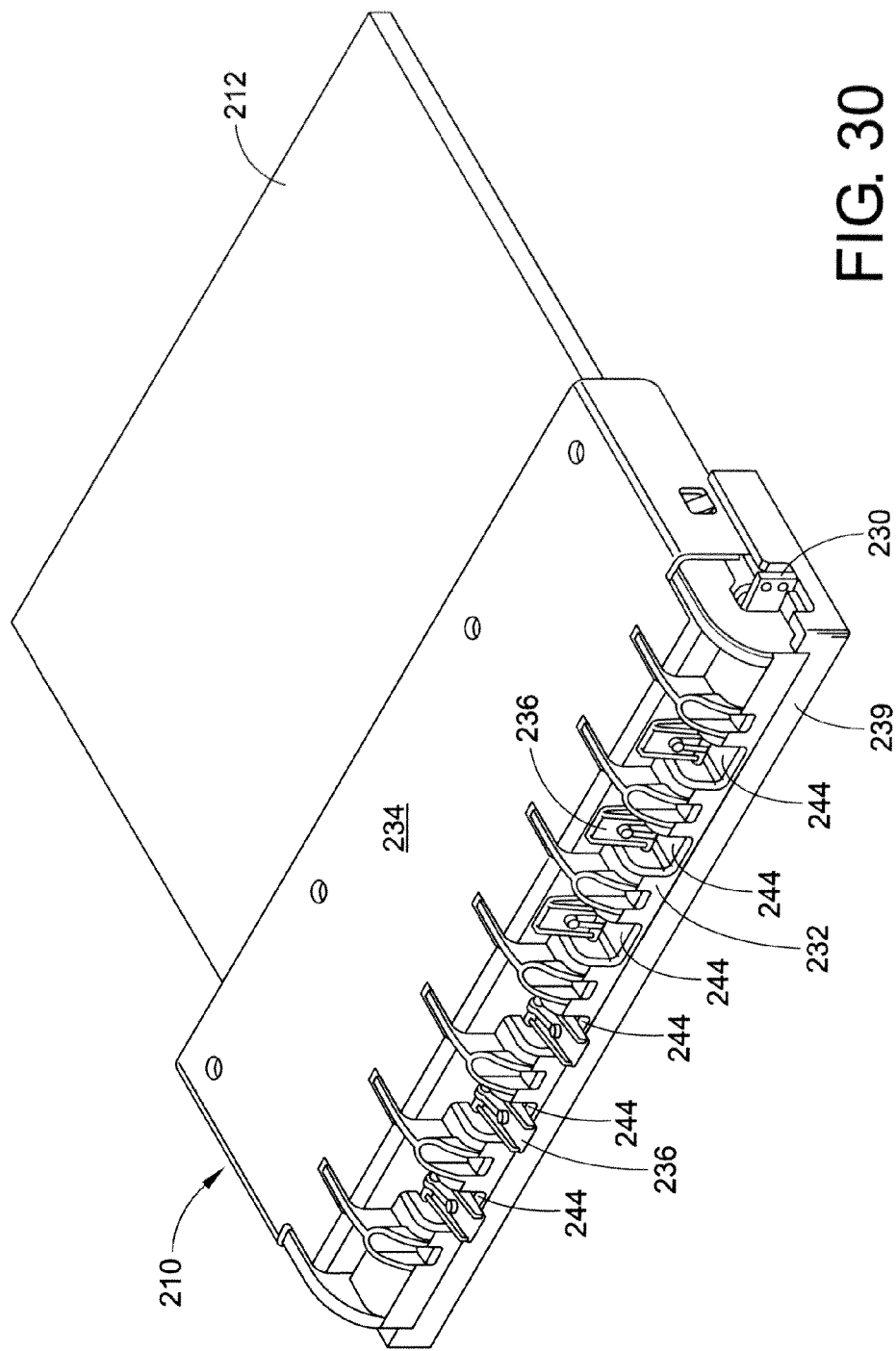
FIG. 30 shows a perspective view of the assembled third embodiment.
Figure 32:
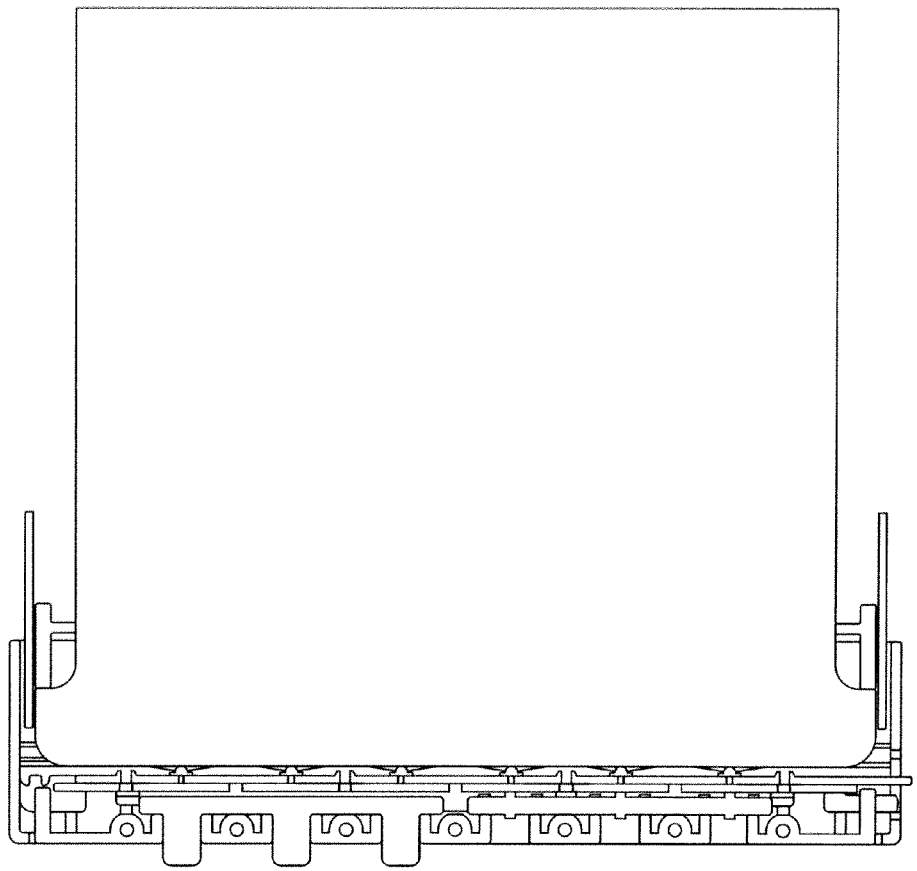
FIG. 32 shows a top view in cross-section of he third embodiment.

Optionally, the alignment of the light module 110 connected with the edge 114 of the panel 112 may also define a fixed position of the light module 110 along the edge 114 of the panel 112. This is the purpose of the edge locking levers 136' whose operation is illustrated in FIGS. 27 and 28. These edge locking levers 136' are structurally identical with the locking levers 136 that engage the proximate main side of the panel 112, but lock onto edges of the panel transverse to and at the opposite ends of the edge 114 to which the light module 110 connects. As shown by the omission of one edge locking lever, the shafts 50 of the edge locking levers fit into mating features 164 at ends of the structural support body 132. Operation of the edge locking levers 136' is identical with operation of the levers 136 except that the edge locking levers 136' are oriented to pivot in the plane of the panel 112 and their locking cams 152 engage edges of the panel 112 on either side of the edge 114 to which the light module 110 connects. The opposing forces provided by the two edge locking levers 136' serves to define a fixed (e.g., centered) position of the light module 110 along the edge 114 of the panel 112. Optionally, the edge 114 of the panel 112 may include features such as illustrative protrusions 168 that ensure the panel 112 cannot disengage from the levers 136' once they are locked.

The precise positioning of the LED devices 16, 116 respective to the edge 14, 114 of the transparent or translucent panel 12, 112, especially in terms of defining a fixed separation between the LED devices and the edge of the panel, ensures that the LED based light module 10, 110 efficiently inject light into the panel 12, 112. The separation can be made small, and optionally individual reflectors can be integrated in the light module to further enhance the light coupling into the panel edge. Accordingly, in some embodiments there is no refractive index-matching material disposed between the LED devices 16, 116 and the edge 14, 114 of the panel 12, 112. Alternatively, it is contemplated to provide such an index-matching material to further enhance light coupling efficiency. If used, the index-matching material may comprise (by way of example) an epoxy having a suitable refractive index that is disposed on the light engine 10, 110 and/or on the edge 14, 114 before the light engine is connected to the edge.

With reference to FIGS. 29-33, a third illustrative embodiment is provided. The light source comprises a light emitting diode (LED) based light module 210 removably mechanically connected to a side of a transparent or translucent flat panel 212 to provide edge injection of light into the flat panel 212. The light module 210 is mounted to inject light into an edge 214 of the flat panel 212.

The LED based light module 210 includes six components: an LED board 230 supporting LED devices 216; a structural support body 232; a heat sink body 234; a plurality of locking levers 236; a reflector 238; and a cover 239.

The LED board 230 comprises a circuit board 240 supporting the LED devices 216. The circuit board 240 is elongated so that it can lie along the edge 214 of the panel 212 with the LED devices 216 distributed along the length of the edge to provide a distribution of the light injected into the edge 214. The LED devices 216 are mounted to circuit board 240 to emit light in the general direction of away from the surface of the circuit board 240, and the circuit board 240 is oriented transverse to the plane of the panel 212. The circuit board 240 supports the LED devices 216 and also provides printed circuitry (not shown) for electrically interconnecting the LED devices 216 in order to be powered by a suitable power source (not shown) connecting with the LED based light module 210 by a pigtail, electrical wires or cable terminating in an electrical connector, a plug designed to snap into a receptacle, or other suitable connection (not shown). While the use of the circuit board 240 provides a convenient package for the electrical wiring, it is also contemplated for the LED devices 216 to be mounted on a support that omits printed circuitry and to instead use chip-to-chip wire bonding or other suitable wiring to electrically interconnect the LED devices 216 on the support.

The reflector 238 is positioned intermediate the LED board 230 and the edge 214 of flat panel 212. The reflector 238 includes reflector cups 241 which receive the LED devices 216. The reflector cups 241 can include a highly reflective surface and can be dimensioned to include a opening adjacent the flat panel 212 having a width substantially equal to a height of edge 214. The reflector cups 241 can be elongated in the longitudinal dimension to enhance the distribution of light entering flat panel 212. The reflector 238 can include a ledge 243 upon which LED board 230 rests and can further include a plurality of retaining projections 245. To further enhance ease of assembly, the reflector 238 may include alignment tabs 247 to be received within locating holes on the LED board 230.

The structural support body 232, the heat sink body 234, and the cover 239 together define the housing or mechanical structure of the LED based light module 210. The heat sink body 234 comprises a thermally conductive material such as aluminum, copper, silver, or so forth, or a combination thereof. Alternatively, in some embodiments the heat sink body 234 may comprise a lightweight former such as a plastic former that is coated by a suitable thermally conductive material such as an electroplated copper layer. The heat sink body 234 includes a plurality of tabs 249 received within gaps 251 in structural support body 232. The LED board 230 mounts inside the heat sink body 234 with the backside of the circuit board 240 contacting the heat sink body 234. As with the first embodiment, thermal conductivity of this interface may be enhanced by making the circuit board 240 a metal core printed circuit board (MCPCB), and/or by using a thermally conductive adhesive, or so forth. The assembly of the heat sink body 234, LED board 230, and structural support body 232 is suitably secured together using screws, rivets, or other fasteners securing via mutually aligned fastener openings, of the respective components. Additionally or alternatively, other fastening approaches such as adhesives, soldering, clamps, or so forth may be employed.

A loose attachment of the panel 212 to the light module 210 is achieved by locating wings 223 of panel 212 into slots 225 in structural support body 232. The locking levers 236 are used to secure the LED based light module 210 to the edge 214 of the panel 212. To accommodate the locking levers 236, the structural support body 232 includes slots 244. Each locking lever 236, includes a shaft 250 that is retained in holes of the structural support body 232 in order to allow the locking lever to pivot about the shaft 250. The locking lever 236 includes a locking cam 252 and a handle 254, with the handle 254 located substantially further away from the pivot 250 as compared with the locking cam 252 in order to provide force multiplication.

With reference to FIG. 31 operation of one of the locking levers 236 that engages the main side of the panel 212 is illustrated. In the open position (top), the locking cam 252 is disengaged from the proximate main side of the heat sink 234. By moving the handle upward, the lever 236 is moved into its locked position (bottom). In the locked position, the locking cam 252 presses against the corresponding tab 249 of heat sink 234 to compress the LED board 230 and reflector 238 against the edge 214 of the panel 212.

Figure 34:
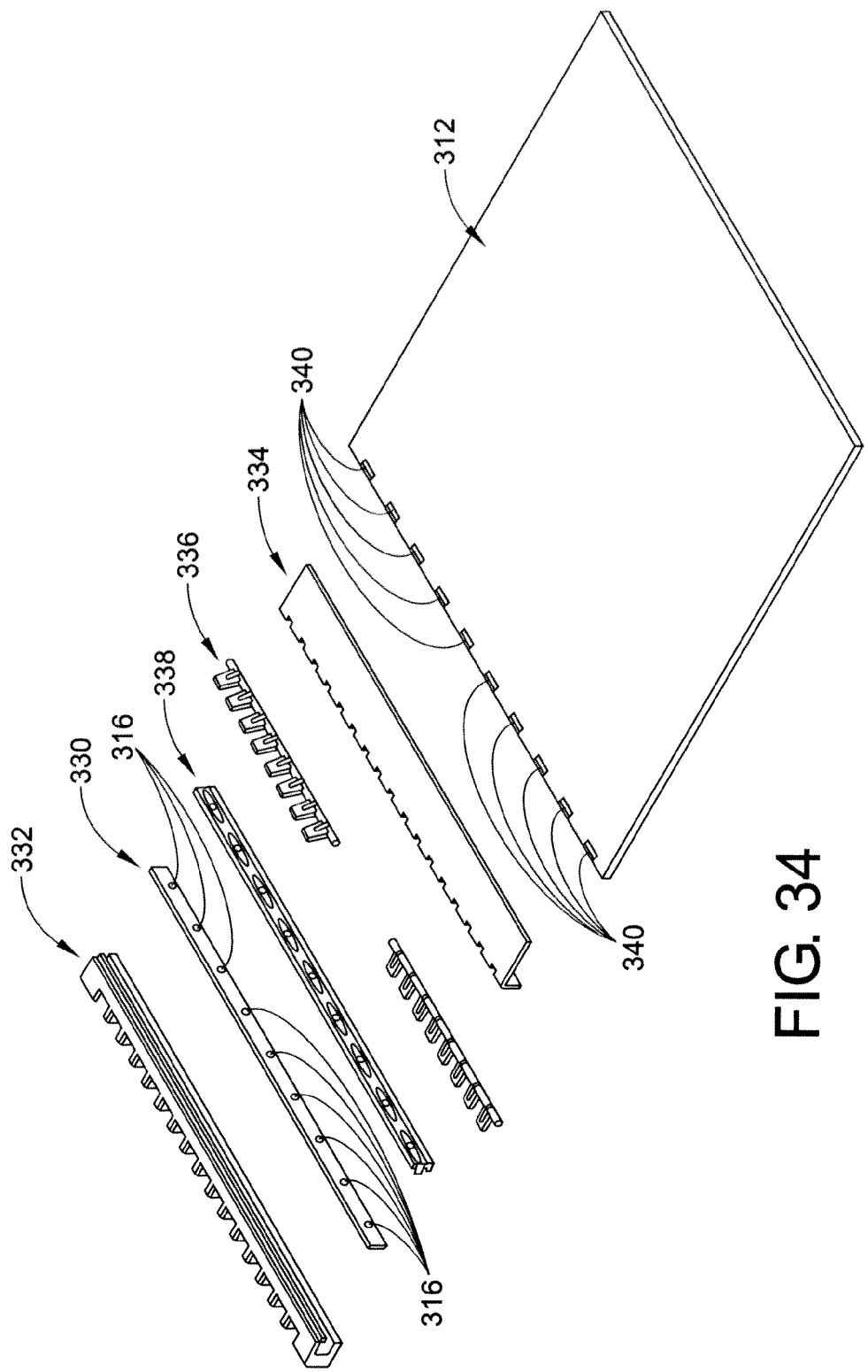
FIG. 34 shows an exploded perspective view of a fourth embodiment.
Figure 36A:
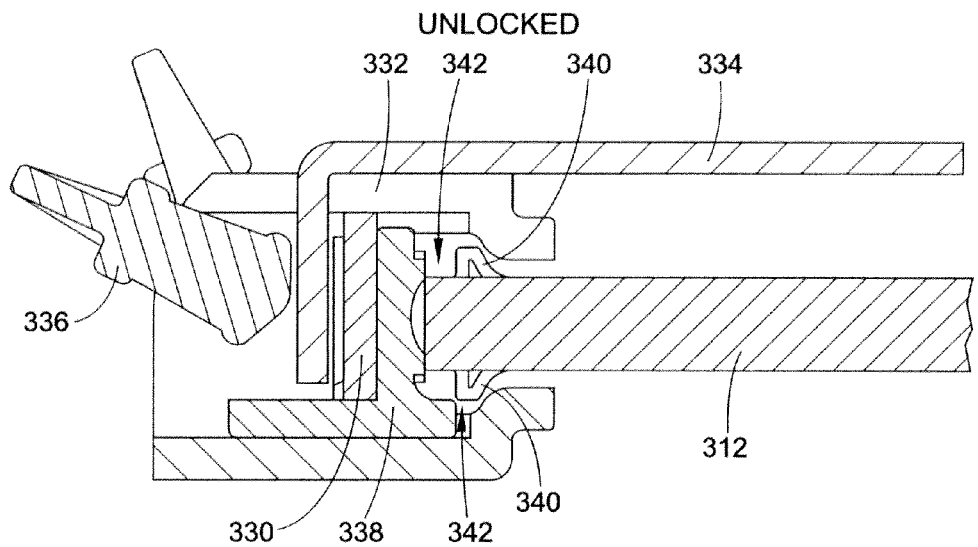
FIGS. 36A and 36B show a diagrammatic side cross-section view illustrating the unlocked and locked positions of the fourth embodiment.
Figure 36B:
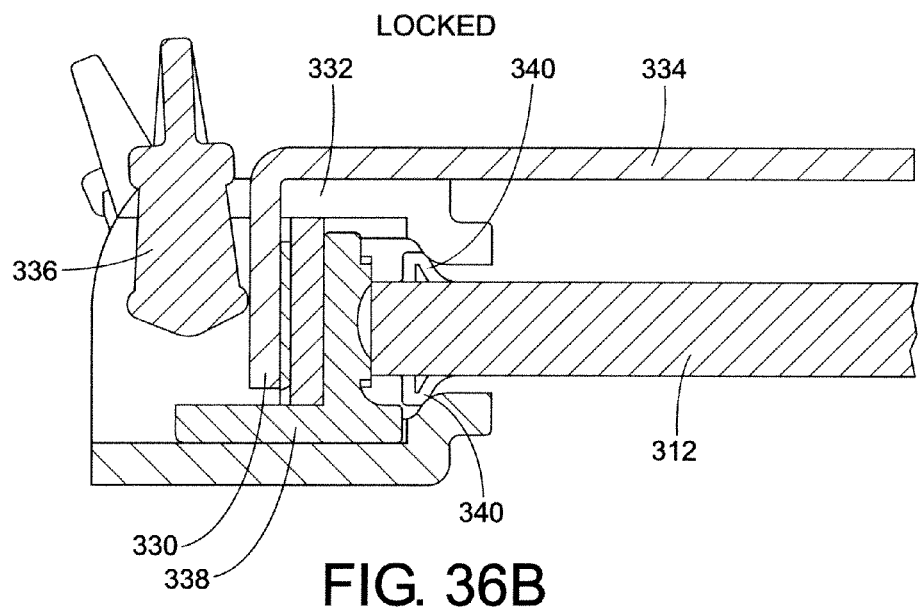

With reference to FIGS. 34-36, a fourth illustrative embodiment depicted. The light source comprises a light emitting diode (LED) based light module 310 removably mechanically connecting to a side of a transparent or translucent flat panel 312 to provide edge injection of light into the flat panel 312. The light module 310 is mounted to inject light into an edge 314 of the flat panel 312. The light module 310 includes LED devices 316.

The LED based light module 310 includes five components: an LED board 330 supporting the LED devices 316; a structural support body 332; a heat sink body 334; a plurality of locking levers 336; and a reflector 338. Embodiment four functions similarly to embodiment three; however, flat panel 312 includes protrusions 340 on each major planar surface adjacent edge 314. Protrusions 340 function to form a loose mated relationship with structural support body 332 as they are retained in channel 342.

The invention claimed is:

1. An apparatus comprising:
a transparent or translucent panel; and
a light module comprising a plurality of light emitting diode (LED) devices, the light module mechanically connected to an edge of the panel by wings, tabs or protrusions disposed on the panel and inserted into the light module and wherein the LED devices are oriented to inject light into the edge of the panel.

2. The apparatus of claim 1, wherein the connection of the light module to the panel defines a fixed position of the light module along the edge of the panel.

3. The apparatus of claim 2, wherein the fixed position of the light module along the edge of the panel is defined by mating connecting features of the LED module and the edge of the panel.

4. The apparatus of claim 1, wherein the light module includes locking levers or clamps compressively locking the light module to the edge of the panel.

5. The apparatus of claim 1, wherein the connection of the light module to the panel defines a fixed separation between the LED devices and the edge of the panel.

6. The apparatus of claim 5, wherein the fixed separation between the LED devices and the edge of the panel is defined by mating connecting features of the LED module and the edge of the panel.

7. The apparatus of claim 5, wherein the fixed separation between the LED devices and the edge of the panel is defined by engagement of the edge of the panel with a stop of the light module.

8. The apparatus of claim 5, wherein the fixed position of the light module along the edge of the panel is defined by engagement of the light module with edges of the panel on either side of the edge of the panel into which the LED devices of the connected light module inject light.

9. The apparatus of claim 1, wherein the light module comprises a circuit board oriented transverse to the panel when the light module is connected with the edge of the panel, the circuit board supporting the LED devices.

10. A light engine module comprising an elongated housing receiving:
a heat sink having a first planar portion and a second at least generally transverse portion;
an elongated printed circuit board hosting a plurality of light emitting diodes (LEDs); and
at least two releasable locking elements comprised of rotatable handles urging said second portion of the heat sink and said printed circuit board into thermal communication.

11. The light engine module of claim 10 wherein said second portion comprises a plurality of tabs.

12. A method comprising:
mechanically connecting a light module to an edge of a transparent or translucent panel via at least two rotatable handles to form a unitary light source, said light module including a plurality of LED devices.

13. The method of claim 12, further comprising:
installing the unitary light source in a fixture.

14. The method of claim 12, further comprising:
installing the unitary light source in a ceiling fixture to define a ceiling light.

15. The method of claim 12, further comprising:
installing the unitary light source as a backlight for a liquid crystal device (LCD) display.

16. A light engine module comprising an elongated housing receiving:
a heat sink having a first planar portion and a second at least generally transverse portion;
an elongated printed circuit board hosting a plurality of light emitting diodes (LEDs);
at least two releasable locking elements urging said second portion of the heat sink and said printed circuit board into thermal communication; and
a transparent or translucent panel, said at least two releasable locking elements urging an edge of said panel into optical communication with said LEDs.

17. The light engine module of claim 16 wherein said housing is comprised of a plastic material and includes an elongated cavity receiving said printed circuit board.

18. The light engine of module claim 16 wherein said housing includes at least one passage receiving said second portion.

19. The light engine module of claim 16 wherein said second portion comprises a plurality of tabs.

20. The light engine module of claim 16 wherein said locking element comprises rotatable handles.

21. The light engine module of claim 16 further comprising, an elongated reflector body including a plurality of reflector cups receiving said LEDs.

22. The light engine module of claim 21 wherein said reflector cups are elongated in a direction of elongation of said reflector body.

* * * * *